United States Patent
Hochgreb et al.

(10) Patent No.: US 10,502,710 B2
(45) Date of Patent: Dec. 10, 2019

(54) PARTICULATE MATTER MEASUREMENT APPARATUS AND METHOD

(71) Applicants: CAMBRIDGE ENTERPRISE LIMITED, Cambridge (GB); ALPHASENSE, LIMITED, Braintree, Essex (GB)

(72) Inventors: Simone Hochgreb, Cambridge (GB); Robert Nishida, Cambridge (GB); Adam Boies, Cambridge (GB); John Saffell, Cambridge (GB)

(73) Assignees: ALPHASENSE LIMITED, Braintree (GB); CAMBRIDGE ENTERPRISE LIMITED, Cambridge (GB)

( * ) Notice: Subject to any disclaimer, the term of this patent is extended or adjusted under 35 U.S.C. 154(b) by 27 days.

(21) Appl. No.: 15/614,992

(22) Filed: Jun. 6, 2017

(65) Prior Publication Data

US 2017/0350862 A1 Dec. 7, 2017

(30) Foreign Application Priority Data

Jun. 6, 2016 (GB) .................................... 1609868.3

(51) Int. Cl.
*G01N 27/62* (2006.01)
*G01N 27/70* (2006.01)
(Continued)

(52) U.S. Cl.
CPC ............. *G01N 27/70* (2013.01); *B03C 3/017* (2013.01); *B03C 3/025* (2013.01); *B03C 3/383* (2013.01);
(Continued)

(58) Field of Classification Search
CPC .... H01J 37/28; H01J 2237/006; H01J 49/062; H01J 2237/0827; H01J 2237/2448;
(Continued)

(56) References Cited

U.S. PATENT DOCUMENTS

| 4,200,609 A | 4/1980 | Byrd |
| 4,574,004 A | 3/1986 | Schmidt-Ott et al. |

(Continued)

FOREIGN PATENT DOCUMENTS

| CN | 203443878 | 2/2014 |
| EP | 0 514 531 | 6/1992 |

(Continued)

OTHER PUBLICATIONS

A. Schmidt-Ott and H. C. Seigman, *Photoelectron emission from small particles suspended in air*, Applied Physics Letters 32 710 (1978) doi: 10.1063/1.89915 (5 pgs.).

(Continued)

*Primary Examiner* — Vinh P Nguyen
(74) *Attorney, Agent, or Firm* — Nixon & Vanderhye P.C.

(57) ABSTRACT

Particle measurement apparatus comprises an inlet for receiving a gas sample for analysis, a photoionisation chamber, at least one light source arranged to illuminate an interior of the photoionisation chamber, first and second electrodes coupled to a power source and configured to provide a DC potential difference across at least a portion of the photoionisation chamber, and an outlet, together defining a gas flow path from the inlet, through the photoionisation chamber, and towards the outlet.

27 Claims, 12 Drawing Sheets

(51) Int. Cl.
- *B03C 3/02* (2006.01)
- *G01N 15/02* (2006.01)
- *G01N 15/06* (2006.01)
- *G01N 15/10* (2006.01)
- *B03C 3/017* (2006.01)
- *B03C 3/38* (2006.01)
- *B03C 3/47* (2006.01)
- *B03C 3/49* (2006.01)

(52) U.S. Cl.
CPC ............ *B03C 3/47* (2013.01); *B03C 3/49* (2013.01); *G01N 15/0266* (2013.01); *G01N 15/0656* (2013.01); *G01N 15/1031* (2013.01); *G01N 15/0606* (2013.01)

(58) Field of Classification Search
CPC ........... H01J 37/3007; H01J 37/305; H01J 37/32082; H01J 49/0027; H01J 2237/043; H01J 2237/063; G01N 27/622; G01N 15/0266; G01N 27/02; G01N 27/021; G01N 27/12; G01N 27/227; G01N 15/0618; G01N 15/0656; G01N 15/1031; G01N 1/2202; G01N 1/40; G01N 27/00; G01N 27/62; G01N 27/624; G01N 27/64; G01N 27/68; G01N 27/70; G06F 19/00
USPC .......................................... 324/464
See application file for complete search history.

(56) References Cited

U.S. PATENT DOCUMENTS

| | | |
|---|---|---|
| 4,790,650 A | 12/1988 | Keady |
| 4,837,440 A | 6/1989 | Burtscher et al. |
| 5,118,959 A | 6/1992 | Caldow et al. |
| 5,153,519 A * | 10/1992 | Wentworth ............ G01N 27/70 324/123 R |
| 5,431,714 A | 7/1995 | Burtscher et al. |
| 5,498,271 A | 3/1996 | Marple et al. |
| 6,230,572 B1 | 5/2001 | Pui et al. |
| 6,639,671 B1 | 10/2003 | Liu |
| 6,993,955 B1 | 2/2006 | King et al. |
| 7,812,306 B2 * | 10/2010 | Fissan ............ G01N 23/00 250/281 |
| 2006/0150754 A1 | 7/2006 | Burtscher et al. |
| 2006/0284077 A1 | 12/2006 | Fissan et al. |
| 2011/0018546 A1 * | 1/2011 | Kitano ............ G01N 27/68 324/464 |
| 2011/0216317 A1 | 9/2011 | Marra |
| 2011/0220811 A1 | 9/2011 | Dick et al. |
| 2012/0304738 A1 | 12/2012 | Landkammer |
| 2013/0265574 A1 | 10/2013 | Buckley et al. |
| 2014/0069169 A1 * | 3/2014 | Janka ............ G01N 1/2252 73/28.02 |
| 2014/0083167 A1 | 3/2014 | Liu |
| 2014/0247450 A1 | 9/2014 | Han |
| 2014/0255283 A1 | 9/2014 | Sidheswaran et al. |
| 2014/0339415 A1 | 11/2014 | Caldow et al. |
| 2015/0093294 A1 | 4/2015 | Hingorani et al. |
| 2016/0305872 A1 | 10/2016 | Kaye et al. |

FOREIGN PATENT DOCUMENTS

| | | |
|---|---|---|
| EP | 1 156 320 B1 | 4/2008 |
| EP | 1 965 192 A1 | 9/2008 |
| EP | 1 655 595 B1 | 10/2009 |
| EP | 2 606 344 | 2/2012 |
| EP | 2 666 007 | 7/2012 |
| GB | 2 346 700 | 8/2000 |
| GB | 2 374 671 | 6/2003 |
| GB | 2 378 510 | 10/2003 |
| GB | 2 416 913 | 2/2006 |
| WO | WO 2007/000710 | 1/2007 |
| WO | WO 2009/074910 | 6/2009 |
| WO | 2012/127104 | 9/2012 |
| WO | WO 2012/142297 | 10/2012 |
| WO | 2013/083879 | 6/2013 |
| WO | 2013/121094 | 8/2013 |
| WO | 2013/121095 | 8/2013 |
| WO | 2013/121096 | 8/2013 |
| WO | WO 2013/121115 | 8/2013 |
| WO | 2013/132154 | 9/2013 |
| WO | 2014/033040 | 3/2014 |

OTHER PUBLICATIONS

Scheuch Dry Electrostatic Precipitators for Flue Gas Dedusting (Brochure), date unknown (12 pgs.).

* cited by examiner

PARTICULATE MATTER MEASUREMENT APPARATUS AND METHOD

This application claims priority to GB Patent Application No. 1609868.3 filed 06 Jun. 2016, the entire content of which is hereby incorporated by reference.

FIELD OF THE INVENTION

Particle measurement apparatus and methods for determining concentration and size parameters of particles in a gas sample.

BACKGROUND TO THE INVENTION

Particle sensors (i.e. particulate matter sensors) are used in a wide range of fields to detect and measure particles suspended in a gas (i.e. an aerosol). Of particular interest is the detection of soot particles, which generally comprise elemental or black carbon, formed during the combustion of fossil fuels in vehicles and during power generation, and which are known to have a negative impact on human health. Many larger particles may be detected using optical sensors. However, the detection and characterisation of particles having diameters below 300 nm is becoming increasingly important. These particles account for more than 90% of airborne particles and reach concentrations of $10^4$ $cm^{-3}$ to $10^5$ $cm^{-3}$ in urban environments. The human health effects caused by, for example, inhalation of such nanoscale particles are potentially worse than those cause by inhalation of larger particles and this is currently under investigation.

Particle distributions in a gas sample may be characterised in many different ways. For example, particle sensors may be used to determine: the total particle mass per unit gas volume for particles within a given size (e.g. diameter) range; the particle number per unit gas volume (i.e. the particle concentration); or the particle surface area per unit gas volume. With regard to human health, it is also possible to measure an effective particle surface area per unit gas volume dependent on the particular health effect being considered. For example, determination of a particle lung-deposited surface area taking into account the variable lung-deposition probability of particles of different sizes within a distribution has been proposed.

Known sub-micron particle sensors, and particularly known particle sensors capable of detecting particles having diameters less than 300 nm, are based on a diffusion charging mechanism. In such devices, a bipolar or unipolar diffusion charger is used to electrically charge particles in a gas sample and thus to allow classification and/or detection of the particles. Such devices are typically large and/or expensive and/or accurate only under idealised conditions. In addition, particle charging by the diffusion mechanism is inefficient, particularly for smaller particles less than 50 nm in diameter. It would therefore be beneficial to provide a particle sensor which is more compact, which is cheaper both to manufacture and to operate, and which is still capable of detecting and characterising particles having diameters less than 300 nm.

SUMMARY OF THE INVENTION

A first aspect of the invention provides particle measurement apparatus (e.g. for determining concentration and/or size parameters of particles in a gas sample). The apparatus comprises an inlet for receiving a gas sample for analysis, a photoionisation chamber, at least one (ultraviolet) light source arranged to illuminate an interior of the photoionisation chamber, first and second electrodes coupled to a power source and configured to provide (in use) a DC (electric) potential difference across at least a portion of (the interior of) the photoionisation chamber (thereby forming an ion and/or charged particle trap), and an outlet, together defining (in use) a gas flow path from the inlet, through the (interior of the) photoionisation chamber, and towards the outlet.

It may be that the at least one (ultraviolet) light source is provided (i.e. located) within the (interior of the) photoionisation chamber.

It may be that the at least one (ultraviolet) light source is arranged to direct (i.e. shine) (ultraviolet) light into the (interior of the) photoionisation chamber. For example, it may be that the at least one (ultraviolet) light source is provided (i.e. located) outside the (interior of the) photoionisation chamber, said at least one (ultraviolet) light source being arranged to direct (i.e. shine) (ultraviolet) light into the (interior of the) photoionisation chamber.

In use, the gas sample to be analysed typically flows through (e.g. is pumped through) the inlet and into and through the (interior of the) photoionisation chamber. Some of the light emitted by the light source within the (interior of the) photoionisation chamber, and/or directed by the light source into the (interior of the) photoionisation chamber, is absorbed by some of the particles in the gas sample, typically causing photoionisation of said particles within the photoionisation chamber. The particles typically emit negatively charged photoelectrons on photoionisation, the particles thereby acquiring a net positive charge. Some or all of the emitted photoelectrons may combine with gas molecules in the sample gas in the photoionisation chamber, thereby forming negatively charged ions. The gas sample flowing through the photoionisation chamber therefore typically comprises a mixture of neutral gas molecules, neutral and positively charged particles, negatively charged photoelectrons and negatively charged gas ions. This mixture typically flows through the potential difference provided between the first and second electrodes across at least a portion of the photoionisation chamber. Indeed, photoionisation of the particles in the sample gas typically occurs within the potential difference between the first and second electrodes. For a given applied potential difference, positively charged particles in the flow of sample gas typically drift towards (i.e. are deflected towards) one of the first and second electrodes (i.e. the one of the first and second electrodes functioning as a cathode), while negatively charged photoelectrons and ions typically drift towards (i.e. are deflected towards) the other of the first and second electrodes (i.e. the one of the first and second electrodes functioning as an anode), under the influence of the potential difference. As the particles are typically substantially less mobile than either the photoelectrons or the negatively charged ions, the photoelectrons and the negatively charged ions will typically drift towards the anode much faster and are more likely to contact a surface of the anode before they can flow out of the photoionisation chamber. In contrast, the positively charged particles are typically unlikely (or at least less likely) to reach or contact a surface of the cathode before they flow out of the photoionisation chamber. Consequently, the first and second electrodes typically function together as an ion trap capturing electrons and negatively charged ions and removing them from the flow of gas and charged particles. Positively charged particles typically flow out of the photoionisation chamber towards the outlet.

By applying a DC potential difference across the first and second electrodes, thereby forming an ion trap, negatively charged ions and photoelectrons are removed from the flow of sample gas. This reduces (preferably prevents) recombination of ions with positively charged particles (resulting in neutrally charged gas molecules and particles) within the photoionisation chamber. Recombination of gas ions and charged particles generated by photoionisation of the gas sample typically degrades any detected signal in known photoionisation-based particle sensors, reducing their accuracy. In contrast, photoionisation of the particles in the gas sample in the present invention is enhanced and recombination is reduced. One consequence is that any detected signal is also enhanced. Another consequence is that any detected signal is more representative of the surface area of particles in the gas. Accordingly, the particle detector is more accurate. In addition, by arranging the first and second electrodes such that the potential difference may be applied directly across the photoionisation chamber, manufacture of a smaller, more compact particle measurement apparatus is made possible.

Because photoionisation of smaller particles, such as particles having diameters less than 50 nm, is a more efficient process than charging such particles by, for example, corona discharge methods, smaller particles are also typically detected more effectively by the particle measurement apparatus of the present invention.

Throughout this specification and the appended claims, it will be understood that a DC potential difference (or a DC voltage) is defined with reference to a DC current, i.e. a direct current (a direct current comprising a unidirectional flow of charge). A DC potential difference (voltage) is a potential difference (voltage) which causes a DC current to flow in a conductor across which it is applied. In particular, we mean that a DC potential difference (DC voltage) is not an AC potential difference (or an AC voltage) (as might be applied across a photoionisation chamber in order to measure photoconductivity, for example), i.e. a DC potential difference (DC voltage) is not an alternating potential difference (voltage). A DC potential difference (DC voltage) is not a harmonic (i.e. harmonically oscillating) potential difference (voltage) (as might be applied across a photoionisation chamber in order to measure photoconductivity, for example).

It may be that the DC potential difference (voltage) is substantially constant. The DC potential difference (voltage) may be substantially constant over a given period of time. The DC potential difference (voltage) may be substantially constant for the duration of a measurement of a particle concentration and/or size parameter. The DC potential difference (voltage) may be substantially constant for a period of time immediately preceding a measurement of a particle concentration and/or size parameter.

The DC potential difference (voltage) may be substantially constant for a period of time greater than a residence time of a particle in the gas sample in the photoionisation chamber. The DC potential difference (voltage) may be substantially constant for a period of time greater than a residence time of a particle in the gas sample between the first and second electrodes. The DC potential difference (voltage) may be substantially constant for a period of time greater than a residence time of a particle in the gas sample in the DC potential difference (voltage), i.e. in the electric field provided by said DC potential difference (voltage).

The DC potential difference (voltage) may be stepped. The DC potential difference (voltage) may be stepped between two or more substantially constant DC voltages. It may be that the DC potential difference (voltage) is stepped between two or more substantially constant DC voltages, thereby forming a square wave potential (voltage).

It may be that the DC potential difference (voltage) is a variable potential difference (voltage). It may be that the DC potential difference (voltage) is a potential difference (voltage) which varies in use around a local, non-zero mean value. However, the DC potential difference (voltage) does not typically alternate significantly over timescales of interest, and more specifically, the DC potential difference (voltage) does not alternate substantially cyclically (e.g. sinusoidally) about a zero voltage. If the DC potential difference (voltage) varies, it does not typically change polarity as it varies.

Gas ions and/or photoelectrons and/or charged particles trapped by the electrodes functioning as an ion trap typically contribute to an electrode current flowing to or from at least one of the first and second electrodes (e.g. flowing between said first and second electrodes). The electrode current typically arises from charged gas ions and/or photoelectrons and/or charged particles reaching at least one of the first and second electrodes as a result of the DC potential difference applied therebetween.

Consequently, the apparatus may further comprise electrode current measuring means (for example, one or more electrode current sensors) configured to measure (in use) the electrode current flowing to or from at least one of the first and second electrodes (e.g. flowing between the first and second electrodes). Parameters indicative of the concentration and size of the particles in the gas sample (for example, a total effective surface area of particles in the gas sample) may be determined from the measured electrode current.

It may be that the electrode current measuring means (e.g. one or more electrode current sensors) comprises at least one of the following: an ammeter (for example, a picoammeter or a femtoammeter); a galvanometer; a resistor (for example, a shunt resistor) coupled to a voltmeter. It may be that the electrode current measuring means comprises any other electrical, electromagnetic or electromechanical devices known in the art for measuring electrical currents.

It may be that the electrode current measuring means (e.g. one or more electrode current sensors) is configured to output a signal (e.g. a digital signal) indicative of the electrode current. It may be that the apparatus is configured to (e.g. calibrated to) output a signal (e.g. a digital signal) indicative of a particle concentration and/or size parameter determined based on the measured electrode current. For example, it may be that the apparatus comprises at least one processor (in electronic communication with a memory storing computer executable program code) configured to (e.g. programmed to) output a signal (e.g. a digital signal) indicative of a particle concentration and/or size parameter determined based on the measured electrode current.

The apparatus may further comprise a charged particle detector. The charged particle detector is typically provided downstream of the photoionisation chamber (i.e. between the photoionisation chamber and the outlet). In use, the gas sample flowing through the apparatus typically flows from the photoionisation chamber, through the charged particle detector and towards the outlet. It may be that the gas sample flows over (a detecting surface of) the charged particle detector as it flows from the photoionisation chamber towards the outlet. It may be that the gas sample flows onto (a detecting surface of) the charged particle detector as it flows from the photoionisation chamber towards the outlet.

The charged particle detector is typically configured to detect (in use) charged particles from the gas sample. It may be that the charged particle detector is configured to detect (in use) positively charged particles from the gas sample. It may be that the charged particle detector is a charged particle and ion detector configured to detect both charged particles and ions from the sample gas. It may be that the charged particle detector is a charged particle collector configured to collect charged particles from the gas sample. It may be that the charged particle detector is a charged particle and ion collector configured to collect charged particles and ions from the gas sample.

The charged particle detector may comprise a Faraday cup, configured to collect charged particles (and/or ions and/or electrons) incident thereon from the sample gas. The Faraday cup typically generates (e.g. outputs) a detector current when charged particles (and/or ions and/or electrons) are incident thereon. The charged particle detector may comprise a Faraday cage, configured to detect charged particles (and/or ions and/or electrons) passing therethrough. A detector current is typically induced in the Faraday cage as charged particles (and/or ions and/or electrons) pass therethrough.

The charged particle detector may comprise a Faraday cup electrometer. The Faraday cup electrometer may comprise a charged particle filter provided within a wire mesh (i.e. within a Faraday cage). The charged particle filter may be an electrically conductive charged particle filter (e.g. a filter formed from electrically conductive fibres). The Faraday cup electrometer typically generates a detector current when charged particles (and/or ions and/or electrons) are incident on the charged particle filter within the wire mesh (e.g. Faraday cage).

The charged particle detector may comprise a particle trap. The particle trap may be formed by a trap potential difference applied between a first trap electrode and a second trap electrode. The applied trap potential difference is typically large enough to cause any charged particles passing between the first and second trap electrodes to be attracted towards and captured by one or the other of said first and second trap electrodes. The first and second trap electrodes may be configured (e.g. positioned) to provide the trap potential difference across a portion of the photoionisation chamber (e.g. downstream of the first and second electrodes).

The apparatus may further comprise detector current measuring means (e.g. one or more detector current sensors) configured to measure a detector current flowing to or from the charged particle detector. Parameters indicative of the concentration and size of the particles in the gas sample (for example, a total effective surface area of particles in the gas sample) may be determined from the measured detector current.

It may be that the detector current measuring means (e.g. one or more detector current sensors) comprises at least one of the following: an ammeter (for example, a picoammeter or a femtoammeter); a galvanometer; a resistor (for example, a shunt resistor) coupled to a voltmeter. It may be that the detector current measuring means comprises any other electrical, electromagnetic or electromechanical devices known in the art for measuring electrical currents.

It may be that the detector current measuring means (e.g. one or more detector current sensors) is configured to output a signal (e.g. a digital signal) indicative of the detector current. It may be that the apparatus is configured to (e.g. calibrated to) output a signal (e.g. a digital signal) indicative of a particle concentration and/or size parameter determined based on the measured detector current. For example, it may be that the apparatus comprises at least one processor (in electronic communication with a memory storing computer executable program code) configured to (e.g. programmed to) output a signal (e.g. a digital signal) indicative of a particle concentration and/or size parameter determined based on the measured detector current.

It may be that the electrode current and the detector current are substantially similar. It may be that the variation of (e.g. the dependence of) the electrode current with (on) the applied potential difference is substantially similar to the variation of (dependence of) the detector current.

It may be that the apparatus comprises either electrode current measuring means or detector current measuring means. Alternatively, it may be that the apparatus comprises both electrode current measuring means and detector current measuring means.

The apparatus may further comprise a comparator circuit configured to compare the electrode current (measured by the electrode current measuring means) and the detector current (measured by the detector current measuring means). It may be that the comparator circuit is configured to output a signal (e.g. a digital signal) indicative of a result determined by comparing the electrode current and the detector current (for example a difference between the electrode current and the detector current). It may be that the comparator circuit is configured to (e.g. calibrated to) output a signal (e.g. a digital signal) indicative of a particle concentration and/or size parameter. By measuring and comparing both the electrode current and the detector current, particle concentration and/or size parameters may be determined more accurately than if only one of the electrode current and detector current is measured and/or taken into account.

The apparatus may further comprise a compensation circuit configured to compensate the measured electrode current (and/or the measured detector current) for a background current signal detected when no particles flow through the photoionisation chamber. The compensation circuit may therefore compensate the measured electrode current (and/or the measured detector current) for the effects of photoemission from photoionisation chamber walls.

The apparatus may further comprise at least one processor (in electronic communication with a memory storing computer executable program code) configured (e.g. programmed) to process the electrode current, measured by the electrode current measuring means, and the detector current, measured by the detector current measuring means, to determine at least one particle concentration and/or size parameter. The (at least one) processor (in electronic communication with a memory storing computer executable program code) may be configured (e.g. programmed) to take into account the applied potential difference in determining the at least one particle concentration and/or size parameter. The (at least one) processor may be configured (e.g. programmed) to take into account a background electrode (and/or detector) current signal.

It may be that the potential difference provided by the first and second electrodes is variable between at least first and second different DC voltages. In use, the potential difference provided by the first and second electrodes may be varied between said at least first and second different DC voltages. While the potential difference between the first and second electrodes is held at the first DC voltage, a first electrode current and/or a first detector current is typically measurable. While the potential difference between the first and second electrodes is held at the second DC voltage different from said first DC voltage, a second electrode current different from the first electrode current and/or a second detector current different from the first detector current is typically measurable. The electrode and/or detector currents typically change on variation of the applied potential difference because the rate at which photoelectrons, negatively charged ions and/or positively charged particles drift towards either of the first and/or second electrodes depends on the magnitude of the potential difference therebetween. For example, when a greater potential difference is applied, photoelectrons, negatively charged ions and/or positively charged particles typically drift more quickly towards the first and/or second electrodes than when a smaller potential difference is applied, such that more of said photoelectrons, negatively charged ions and/or potentially positively charged particles are captured by the ion trap, thereby contributing to an increased electrode current. The detector current may be either increased or reduced by an increase in the applied potential difference, as an increase in the potential difference can result in greater trapping of both gas ions (reducing recombination and thus increasing the number of charged particles which reach the detector) and charged particles (reducing the number of charged particles which reach the detector). By measuring and comparing the first electrode current, the second electrode current, the first detector current and/or the second detector current, parameters relating to the concentration and size of the particles in the gas sample may be determined more accurately than when, for example, currents are measured during application of one single potential difference only (or when no potential difference is applied). In addition, the inventors have found that by measuring and comparing the first electrode current, the second electrode current, the first detector current and the second detector current, both the particle concentration and the mean diameter of particles in the gas sample may be determined independently (from one set of measurements, e.g. simultaneously). The dependence of the measured electrode and detector currents on the particle concentration and mean diameter is itself typically dependent on the magnitude and/or polarity of the applied potential difference. In particular, the measured electrode and detector currents typically each display a power-law dependence on both the particle concentration and mean diameter, wherein the exponents of the concentration and the mean diameter are each dependent on the applied potential difference. By varying the applied potential difference between at least first and second voltages, and by using the known relationships between the electrode and detector currents, the particle concentration and mean diameter, and the potential difference-dependent exponents, the particle concentration and the mean diameter may be individually evaluated. In addition, at increasing voltages, greater proportions of the positively charged particles (particularly smaller, more mobile particles) are typically likely to be captured by the ion trap and so measuring the electrode and detector currents at least two different applied voltages may also provide more detailed information on the size and/or mass (e.g. a size and/or mass distribution) of the particles, if at least one of said applied voltages is sufficiently high so that some particles are captured by the trap. The present invention therefore results in more accurate particle measurement apparatus, as well as apparatus more able to determine a wider range of particle size parameters, as well as apparatus able to determine particle concentration and mean particle diameter independent of one another (from the same set of measurements), as well as apparatus able to determine a particle size and/or mass distribution.

It may be that each of the at least first and second DC voltages have the same polarity. For example, it may be that varying the potential difference between the first and second electrodes from the first DC voltage to the second DC voltage, or vice versa, does not change the polarity of the potential difference. In such embodiments, varying the potential difference between the first and second DC voltages does not change the (principal) direction in which negatively charged ions and/or photoelectrons and/or positively charged particles drift within said potential difference (i.e. varying the potential difference does not change which of the first and second electrodes negatively charged ions and/or photoelectrons and/or positive charged particle drift towards).

It may be that some or each of the at least first and second DC voltages have different polarities. For example, it may be that varying the potential difference between the first and second electrodes from the first DC voltage to the second DC voltage, or vice versa, switches the polarity of the potential difference. In such embodiments, varying the potential difference between the first and second DC voltages switches the (principal) direction in which negatively charged ions and/or photoelectrons and/or positively charged particles drift within said potential difference (i.e. varying the potential difference switches which of the first and second electrodes negatively charged ions and/or photoelectrons and/or positive charged particle drift towards).

It may be that one of the at least first and second DC voltages is a zero voltage. In such embodiments, each of the other(s) of the at least first and second DC voltages is typically a non-zero voltage. Alternatively, it may be that none of the at least first and second DC voltages is a zero voltage.

It may be that the applied DC potential causes fewer than 30%, or more typically fewer than 20%, or more typically fewer than 10%, of the charged particles in the gas flow to be captured by the ion trap.

It may be that the magnitudes of the first and second DC voltages differ by a factor of at least 2, or more typically at least 5, or more typically at least 10. For example, it may be that the magnitude of the second DC voltage is greater than the magnitude of the first DC voltage by a factor of at least 2, or at least 5, or at least 10. A greater difference in magnitude between the first and second DC voltages typically results in a greater difference in electrode and/or detector currents measured at the said first and second DC voltages and consequently a more accurate determination of the particle concentration and/or size parameters (and, in particular, the mean particle diameter).

It may be that the potential difference provided by the first and second electrodes is variable (in use) between a plurality of different DC voltages (the plurality of different DC voltages typically comprising the at least first and second different DC voltages). For example, it may be that the potential difference provided by the first and second electrodes is variable (in use) between first, second and third different DC voltages. It may be that the potential difference provided by the first and second electrodes is variable (in use) between first, second, third and fourth different DC voltages. It may be that the potential difference provided by the first and second electrodes is variable (in use) between first, second, third, fourth and fifth different DC voltages. It may be that the potential difference provided by the first and second electrodes is variable (in use) between at least six different DC voltages. It may be that the potential difference provided by the first and second electrodes is variable (in use) between at least eight different DC voltages. It may be that the potential difference provided by the first and second electrodes is variable (in use) between at least ten different DC voltages. It may be that the potential difference provided by the first and second electrodes is variable (in use) between at least twelve different DC voltages. The greater the number of different DC voltages between which the potential difference is variable, the greater the number of different electromotive forces which may be applied to negatively charged ions and/or photoelectrons and/or positively charged particles in the ion trap, the greater the number of different electrode currents and detector currents which may be measured in use, and thus the more accurately the particle concentration and mean particle diameter, or the more detailed the size distribution of particles within the gas sample, which may be determined.

It may be that the potential difference provided by the first and second electrodes is variable (in use) between at least first and second different steady-state DC voltages. It may be that the potential difference provided by the first and second electrodes is variable (in use) between a plurality of different steady-state DC voltages. Each steady-state DC voltage is typically a DC voltage held substantially constant (e.g. continuously) for a time period of sufficient length such that ion and/or photoelectron and/or charged particle drift (rates) within the ion trap reaches a steady state. For example, each steady-state DC voltage may be a DC voltage held substantially constant for a time period of sufficient length such that ion and/or photoelectron and/or charged particle drift rates within the ion trap approach within 30%, or more typically within 20%, or even more typically within 10%, of their steady-state (i.e. long-time) values (other factors being constant).

It may be that the potential difference provided by the first and second electrodes is maintainable (substantially constantly, i.e. substantially continuously) (in use) at any one of the at least first and second DC voltages for at least 0.1 seconds, or more typically at least 0.25 seconds, or more typically at least 0.5 seconds, or more typically at least 1 second, or even more typically at least 1.5 seconds.

It may be that the potential difference provided by the first and second electrodes is variable (in use) between the at least first and second different DC voltages at a frequency of less than 10 Hz, or more typically less than 5 Hz, or more typically less than 2 Hz, or more typically less than 1 Hz, or even more typically less than 0.5 Hz.

The light source is typically configured to emit light within a specified range of wavelengths. It may be that the light source is an ultraviolet light source configured to emit ultraviolet light. Ultraviolet light has a wavelength of between 10 nm and 400 nm. The ultraviolet light source may be configured to emit ultraviolet light having (substantially) one wavelength. The ultraviolet light source may be configured to emit light having a plurality of wavelengths. The ultraviolet light source may be configured to emit light have a range of wavelengths. The ultraviolet light source is typically configured to emit light having a wavelength (or a plurality of wavelengths, e.g. a range of wavelengths) within the range of 150 nm to 260 nm. It may be that the wavelength of (ultraviolet) light the (ultraviolet) light source is configured to emit is selected based on the known (chemical) composition of the particles whose concentration and size parameters are to be determined. The inventors have found that ultraviolet light having a wavelength of below 150 nm typically ionises sample gas atoms and/or molecules and/or hydrocarbon molecules present in the sample gas, as well as the (soot) particles to be detected, and thus should be avoided. The inventors have found that ultraviolet light having a wavelength of above 260 nm is typically not able to ionise (soot) particles sufficiently for detection.

The (ultraviolet) light source is typically arranged to emit light within the (interior of the) photoionisation chamber, and/or to direct (shine) light into the (interior of the) photoionisation chamber, thereby illuminating (the interior of) said photoionisation chamber with (ultraviolet) light.

It may be that the photoionisation chamber comprises a wall. It may be that the (ultraviolet) light source is provided outside the photoionisation chamber. It may be that the (ultraviolet) light source is arranged to direct (shine) light into the photoionisation chamber through one or more apertures in the wall. It may be that the wall is at least partially (ultraviolet) light permeable and that the (ultraviolet) light source is arranged to direct (shine) light into the photoionisation chamber through the at least partially (ultraviolet) light permeable wall. It may be that the wall comprises one or more at least partially (ultraviolet) light permeable windows, and that the (ultraviolet) light source is arranged to direct (shine) light into the photoionisation chamber through at least one of the one or more at least partially (ultraviolet) light permeable windows.

It may be that the (ultraviolet) light source is provided (i.e. located) within the (interior of the) photoionisation chamber. The (ultraviolet) light source is typically arranged to direct, in use, (ultraviolet) light towards the gas sample flowing through the (interior of) the photoionisation chamber. In particular, the (ultraviolet) light source is typically arranged to direct, in use, (ultraviolet) light towards the gas sample flowing through the (interior of the) photoionisation chamber and between the first and second electrodes.

The first and second electrodes may be provided outside the photoionisation chamber. One or both of the first and second electrodes may be provided within the photoionisation chamber. It may be that one or both of the first and second electrodes is provided within (e.g. is integrally formed with) a wall of the photoionisation chamber. It may be that one or both of the first and second electrodes forms at least a portion of one or more walls of the photoionisation chamber. One or both of the first and second electrodes may be a planar (i.e. flat) electrode. One or both of the first and second electrodes may be a curved electrode. One or both of the first and second electrodes may be a coaxial electrode. One or both of the first and second electrodes may be a cylindrical electrode.

The first and second electrodes are typically positioned such that (in use) photoionisation of particles in the sample gas occurs substantially between said first and second electrodes.

It may be that the first and second electrodes are configured to provide (in use) a potential difference across a substantial portion of (the interior of) the photoionisation chamber. It may be that the first and second electrodes are configured to provide (in use) a potential difference across a majority of (the interior of) the photoionisation chamber. It may be that the first and second electrodes are configured to provide (in use) a potential difference across a substantial portion of (e.g. a majority of) a width of (the interior of) the photoionisation chamber. For example, it may be that the first and second electrodes are configured to provide (in use) a potential difference across at least 50%, more typically 60%, even more typically 70%, even more typically 80%, even more typically 90%, of a volume of (the interior of) the photoionisation chamber. It may be that the first and second electrodes are configured to provide (in use) a potential difference across at least 50%, more typically 60%, even more typically 70%, even more typically 80%, even more typically 90%, of the width of (the interior of) the photoionisation chamber. It may be that the first and second electrodes are configured to provide (in use) a potential difference across the entire (interior of) the photoionisation chamber. The greater the volume of the photoionisation chamber across which the potential difference is provided, the greater the proportion of photoelectrons, negatively charged ions and/or positively charged particles generated in the photoionisation chamber which may be captured by the ion trap and thereby contribute to the measured electrode current.

The apparatus may be used to determine a concentration of particles in the gas sample (i.e. the number of particles per unit gas volume). In addition or alternatively, the apparatus may be used to determine size parameters including one or more of the following: an average diameter of particles in the gas sample; a total surface area of particles in the gas sample; the average surface area of particles in the gas sample; a total effective (e.g. available) surface area of particles in the gas sample; an average effective (e.g. available) surface area of particles in the gas sample; a total mass of particles in the gas sample; an average mass of particles in the gas sample. The apparatus may be used to determine a concentration (i.e. the number of particles per unit gas volume) of particles having a given size parameter (or within a given range of size parameters). For example, the apparatus may be used to determine a concentration (i.e. the number of particles per unit gas volume) of particles within particular size 'buckets' or 'bins'. The apparatus may therefore be used to determine a size and/or mass distribution of particles in the gas sample.

A second aspect of the invention provides a method of measuring particles (e.g. determining concentration and/or size parameters of particles) in a gas sample, the method comprising: directing the gas sample through a photoionisation chamber; illuminating the gas sample within the photoionisation chamber; and concurrently applying a DC (electric) potential difference between first and second electrodes across at least a portion of (an interior of) the photoionisation chamber through which sample gas flows.

The method may further comprise the step of: measuring an electrode current flowing to or from at least one of the first and second electrodes (e.g. flowing between the first and second electrodes). By measuring the electrode current as the gas sample flows through the apparatus, concentration and/or size parameters of particles in the gas sample may be determined.

It may be that the electrode current is measured by way of electrode current measuring means (for example, one or more electrode current sensors) comprising at least one of the following: an ammeter (for example, a picoammeter or a femtoammeter); a galvanometer; a resistor (for example, a shunt resistor) coupled to a voltmeter. It may be that the electrode current measuring means comprise any other electrical, electromagnetic or electromechanical devices known in the art for measuring electrical currents.

The method may further comprise the step of: outputting a signal (e.g. a digital signal) indicative of the measured electrode current.

The method may further comprise the step of: outputting a signal (e.g. a digital signal) indicative of a particle concentration and/or size parameter determined from the measured electrode current.

The method may further comprise the step of: directing sample gas exiting the photoionisation chamber towards a charged particle detector.

The charged particle detector is typically provided downstream of the photoionisation chamber (i.e. between the photoionisation chamber and an outlet). In use, the gas sample flowing through the apparatus therefore typically flows from the photoionisation chamber, through the charged particle detector and towards the outlet.

It may be that the step of directing sample gas exiting the photoionisation chamber towards the charged particle detector comprises directing sample gas over and/or onto (a detecting surface of) the charged particle detector as it flows from the photoionisation chamber towards the outlet.

The charged particle detector is typically configured to detect (in use) charged particles from the gas sample. It may be that the charged particle detector is configured to detect (in use) positively charged particles from the gas sample. It may be that the charged particle detector is a charged particle and ion detector configured to detect both charged particles and ions from the sample gas. It may be that the charged particle detector is a charged particle collector configured to collect charged particles from the gas sample. It may be that the charged particle detector is a charged particle and ion collector configured to collect charged particles and ions from the gas sample.

The charged particle detector may comprise a Faraday cup, configured to collect charged particles (and/or ions and/or electrons) incident thereon from the sample gas. The Faraday cup typically generates (e.g. outputs) a detector current when charged particles (and/or ions and/or electrons) are incident thereon. The charged particle detector may comprise a Faraday cage, configured to detect charged particles (and/or ions and/or electrons) passing therethrough. A detector current is typically induced in the Faraday cage as charged particles (and/or ions and/or electrons) pass therethrough.

The charged particle detector may comprise a Faraday cup electrometer. The Faraday cup electrometer may comprise a charged particle filter provided within a wire mesh (i.e. within a Faraday cage). The charged particle filter may be an electrically conductive charged particle filter (e.g. a filter formed from electrically conductive fibres). The Faraday cup electrometer typically generates a detector current when charged particles (and/or ions and/or electrons) are incident on the charged particle filter within the wire mesh (e.g. Faraday cage).

The charged particle detector may comprise a particle trap. The particle trap may be formed by a trap potential difference applied between a first trap electrode and a second trap electrode. The applied trap potential difference is typically large enough to cause any charged particles passing between the first and second trap electrodes to be attracted towards and captured by one or the other of said first and second trap electrodes.

The method may further comprise the step of: measuring a detector current flowing to or from the charged particle detector.

It may be that the detector current is measured by way of detector current measuring means (e.g. one or more detector current sensors) comprising at least one of the following: an ammeter (for example, a picoammeter or a femtoammeter); a galvanometer; a resistor (for example, a shunt resistor) coupled to a voltmeter. It may be that the detector current measuring means comprise any other electrical, electromagnetic or electromechanical devices known in the art for measuring electrical currents.

The method may further comprise the step of: outputting a signal (e.g. a digital signal) indicative of the measured detector current.

The method may further comprise the step of: comparing the measured electrode current and the measured detector current (by way of a comparator circuit, for example).

The method may further comprise the step of: processing the measured electrode current and the measured detector current (by way of a comparator circuit, for example) to determine a particle concentration and/or size parameter (e.g. taking into account the applied potential difference).

The method may further comprise the step of: compensating the measured electrode current and/or the measured detector current (by way of a compensation circuit, for example) for a background current signal detected when no particles flow through the photoionisation chamber. Accordingly, the method may comprise compensating the measured electrode current and/or the measured detector current for the effects of photoemission from photoionisation chamber walls.

The method may further comprise the step of: outputting a signal (e.g. a digital signal) indicative of a particle concentration and/or size parameter determined from the measured electrode current and/or the measured detector current.

The method may further comprise the step of: varying the potential difference between the first and second electrodes across the at least a portion of the photoionisation chamber through which sample gas flows, the potential difference being varied between at least first and second different DC voltages.

It may be that each of the at least first and second DC voltages have the same polarity. For example, it may be that varying the potential difference between the first and second electrodes from the first DC voltage to the second DC voltage, or vice versa, does not change the polarity of the potential difference. In such embodiments, varying the potential difference between the first and second DC voltages does not change the (principal) direction in which negatively charged ions and/or photoelectrons and/or positively charged particles drift within said potential difference (i.e. varying the potential difference does not change which of the first and second electrodes negatively charged ions and/or photoelectrons and/or positive charged particle drift towards).

It may be that some or each of the at least first and second DC voltages have different polarities. For example, it may be that varying the potential difference between the first and second electrodes from the first DC voltage to the second DC voltage, or vice versa, switches the polarity of the potential difference. In such embodiments, varying the potential difference between the first and second DC voltages switches the (principal) direction in which negatively charged ions and/or photoelectrons and/or positively charged particles drift within said potential difference (i.e. varying the potential difference does not change which of the first and second electrodes negatively charged ions and/or photoelectrons and/or positive charged particle drift towards).

It may be that one of the at least first and second DC voltages is a zero voltage. In such embodiments, the other(s) of the at least first and second DC voltages are typically non-zero voltages. Alternatively, it may be that none of the at least first and second DC voltages is a zero voltage.

It may be that the potential difference provided by the first and second electrodes is variable (in use) between a plurality of different DC voltages (the plurality of different DC voltages typically comprising the first and second different DC voltages). For example, it may be that the method comprises varying the potential difference provided by the first and second electrodes between first, second and third different DC voltages. It may be that the method comprises varying the potential difference provided by the first and second electrodes between first, second, third and fourth different DC voltages. It may be that the method comprises varying the potential difference provided by the first and second electrodes between first, second, third, fourth and fifth different DC voltages. It may be that the method comprises varying the potential difference provided by the first and second electrodes between at least six different DC voltages. It may be that the method comprises varying the potential difference provided by the first and second electrodes between at least eight different DC voltages. It may be that the method comprises varying the potential difference provided by the first and second electrodes between at least ten different DC voltages. It may be that the method comprises varying the potential difference provided by the first and second electrodes between at least twelve different DC voltages. The greater the number of different DC voltages between which the potential difference is varied, the greater the number of different electromotive forces which may be applied to negatively charged ions and/or photoelectrons and/or positively charged particles in the ion trap, the greater the number of different of electrode currents and detector currents which may be measured in use, and thus the more accurately the particle size and/or concentration parameters may be determined, and/or the more detailed a size distribution of particles within the sample which may be determined.

It may be that the method comprises varying the potential difference provided by the first and second electrodes between at least first and second different steady-state DC voltages. Each steady-state DC voltage is typically a DC voltage held substantially constant for a time period of sufficient length such that ion and/or photoelectron and/or charged particle drift (rates) within the ion trap reaches a steady state. For example, each steady-state DC voltage may be a DC voltage held substantially constant for a time period of sufficient length such that ion and/or photoelectron and/or charged particle drift rates within the ion trap approach within 30%, or more typically within 20%, or even more typically within 10%, of their steady-state (i.e. long-time) values.

It may be that the method comprises maintaining the potential difference provided by the first and second electrodes (substantially constantly, i.e. substantially continuously) at each of the at least first and second DC voltages for at least 0.1 seconds, or more typically at least 0.25 seconds, or more typically at least 0.5 seconds, or more typically at least 1 second, or even more typically at least 1.5 seconds.

It may be that the method comprises varying the potential difference provided by the first and second electrodes between the at least first and second different DC voltages at a frequency of less than 10 Hz, or more typically less than 5 Hz, or more typically less than 2 Hz, or more typically less than 1 Hz, or even more typically less than 0.5 Hz.

It may be that the step of illuminating the gas sample within the photoionisation chamber comprises illuminating the gas sample with (ultraviolet) light. It may be that the step of illuminating the gas sample within the photoionisation chamber comprises shining (e.g. directing) (ultraviolet) light towards and/or into and/or onto the gas sample (within the photoionisation chamber). It may be that the step of illuminating the gas sample within the photoionisation chamber comprises illuminating the (interior of the) photoionisation chamber The gas sample and/or the (interior of the) photoionisation chamber may be illuminated by a light source (e.g. by an ultraviolet light source). Light (e.g. ultraviolet light) may be directed towards and/or into and/or onto the gas sample from the light source (e.g. from the ultraviolet light source).

It may be that the photoionisation chamber comprises a wall. It may be that the step of illuminating the gas sample within the photoionisation chamber comprises directing (ultraviolet) light into the photoionisation chamber through one or more apertures in the wall. It may be that the wall is at least partially (ultraviolet) light permeable and that the step of illuminating the gas sample within the photoionisation chamber comprises directing (ultraviolet) light into the photoionisation chamber through the at least partially (ultraviolet) light permeable wall. It may be that the wall comprises at least one partially (ultraviolet) light permeable window, and that the step of illuminating the gas sample within the photoionisation chamber comprises shining (e.g. directing) (ultraviolet) light into the photoionisation chamber through one or more of said at least one windows.

It may be that the step of illuminating the gas sample within the photoionisation chamber comprises shining (e.g. directing) (ultraviolet) light onto the gas sample flowing through the photoionisation chamber and (concurrently) between the first and second electrodes.

The first and second electrodes may be provided outside the photoionisation chamber. One or both of the first and second electrodes may be provided within the photoionisation chamber. It may be that one or both of the first and second electrodes is provided within (e.g. is integrally formed with) a wall of the photoionisation chamber. It may be that one or both of the first and second electrodes forms at least a portion of one or more walls of the photoionisation chamber. One or both of the first and second electrodes may be a planar (i.e. flat) electrode. One or both of the first and second electrodes may be a curved electrode. One or both of the first and second electrodes may be a coaxial electrode. One or both of the first and second electrodes may be a cylindrical electrode.

The first and second electrodes are typically positioned such that (in use) photoionisation of particles in the sample gas occurs substantially between said first and second electrodes.

It may be that the step of varying the (electric) potential difference between first and second electrodes across at least a portion of (an interior of) the photoionisation chamber through which sample gas flows comprises varying said potential difference across a substantial portion of (the interior of) the photoionisation chamber. It may be that the step of varying the (electric) potential difference between first and second electrodes across at least a portion of (an interior of) the photoionisation chamber through which sample gas flows comprises varying said potential difference across a majority of (the interior of) the photoionisation chamber. It may be that the step of varying the (electric) potential difference between first and second electrodes across at least a portion of (an interior of) the photoionisation chamber through which sample gas flows comprises varying said potential difference across a substantial portion of a width of (the interior of) the photoionisation chamber. For example, it may be that the step of varying the (electric) potential difference between first and second electrodes across at least a portion of (an interior of) the photoionisation chamber through which sample gas flows comprises varying said potential difference across at least 50%, more typically 60%, even more typically 70%, even more typically 80%, or even more typically 90%, of a volume of (the interior of) the photoionisation chamber. It may be that the step of varying the (electric) potential difference between first and second electrodes across at least a portion of (an interior of) the photoionisation chamber through which sample gas flows comprises varying said potential difference across at least 50%, more typically 60%, even more typically 70%, even more typically 80%, or even more typically 90%, of the width of (the interior of) the photoionisation chamber. It may be that the step of varying the (electric) potential difference between first and second electrodes across at least a portion of (an interior of) the photoionisation chamber through which sample gas flows comprises varying said potential difference across the entire (interior of) the photoionisation chamber. The greater the volume of the photoionisation chamber across which the potential difference is provided, the greater the proportion of photoelectrons, negatively charged ions and/or positively charged particles generated in the photoionisation chamber which may be captured by the ion trap and thereby contribute to the measured electrode current.

It may be that the method steps of the second aspect of the invention are performed in any given order. However, the steps of illuminating the gas sample within the photoionisation chamber and applying a (electric) potential difference between first and second electrodes across at least a portion of (an interior of) the photoionisation chamber through which sample gas flows are typically performed concurrently.

A third aspect of the invention provides particle measurement apparatus (e.g. for determining concentration and/or size parameters of particles in a gas sample), the apparatus comprising an inlet for receiving a gas sample for analysis, a photoionisation chamber, first and second electrodes, at least one light source arranged to illuminate (in use) an interior of the photoionisation chamber between the first and second electrodes, electrode current measuring means (e.g. one or more electrode current sensors) configured to measure (in use) an electrode current flowing to or from at least one of the first and second electrodes (e.g. flowing between said first and second electrodes), and an outlet, together defining a gas flow path from the inlet, through the photoionisation chamber between the first and second electrodes, and towards the outlet.

The inventors have found that by measuring the electrode current flowing to or from said at least one of the first and second electrodes (e.g. by measuring the ion trap current flowing between said first and second electrodes), the concentration and/or size parameter of particles in the gas sample may be determined. The inventors have found that the magnitude of the electrode current (e.g. the ion trap current) is (at least partially) correlated to the surface area of particles in the gas sample even when no potential difference is applied between the first and second electrodes. However, it may be that the first and second electrodes are further configured to apply a DC potential difference across at least a portion of the photoionisation chamber. The inventors have found that the correlation between the magnitude of the electrode current (e.g. the ion trap current) and the surface area of particles in the gas sample is stronger when said DC potential difference is applied between said first and second electrodes across the photoionisation chamber (than when no potential difference is applied thereacross). For example, the inventors have found experimentally that, when there is no applied potential difference between the first and second electrodes, the correlation between the magnitude of the electrode current (e.g. the ion trap current) and the surface area of particles in the gas sample may be quantified by a correlation coefficient (e.g. a Pearson product-moment correlation coefficient) of approximately 0.6 (the correlation coefficient ranging between minimum and maximum values of −1 and 1), while, when a DC potential difference (such as a DC potential difference of approximately 8 V) is applied between the first and second electrodes, the correlation between the magnitude of the electrode current (e.g. the ion trap current) and the surface area of particles in the gas sample may be quantified by a correlation coefficient (e.g. a Pearson product-moment correlation coefficient) of approximately 0.95. It may be that an electrode current (e.g. an ion trap current) still flows when no potential difference is applied between the first and second electrodes in part because of a difference in surface area of the first and second electrodes. Such a difference in surface area may lead to increased gas ion diffusion between the first and second electrodes (irrespective of an applied voltage). The apparatus may therefore by used to determine concentration and size parameters of particles in the gas sample in an approximate manner when no potential difference is applied between the first and second electrodes, or more accurately when a non-zero DC potential difference is applied therebetween.

Consequently, a fourth aspect of the invention provides a method of measuring particles (e.g. determining concentration and/or size parameters of particles) in a gas sample, the method comprising: directing the gas sample through a photoionisation chamber between first and second electrodes; illuminating the gas sample within the photoionisation chamber between the first and second electrodes; and measuring an electrode current flowing to or from one of the first and second electrodes (e.g. flowing between the first and second electrodes). It may be that the method further comprises the step of: applying a DC potential difference between the first and second electrodes across at least a portion of the photoionisation chamber.

It may be that the method steps of the fourth aspect of the invention are performed in any given order.

A fifth aspect of the invention provides particle measurement apparatus (e.g. for determining concentration and/or size parameters of particles in a gas sample), the apparatus comprising an inlet for receiving a gas sample for analysis, a photoionisation chamber, at least one (ultraviolet) light source arranged to illuminate an interior of the photoionisation chamber, a plurality of electrodes coupled to at least one power supply (e.g. by way of a voltage regulation circuit) and configured to provide (in use) at least two concurrent (different) (DC) potential differences across respective portions of (an interior of) the photoionisation chamber, and an outlet, together defining a gas flow path from the inlet, through the photoionisation chamber, towards the outlet.

By providing at least two (different) (DC) potential differences concurrently across at least two different portions of the photoionisation chamber, particles having different sizes and/or masses are typically trapped by different portions of the photoionisation chamber. The apparatus may therefore be used to determine a size distribution of particles in the gas sample.

Each of the at least two potential differences may be the same (as one another). Alternatively, some or all of the at least two potential differences may be different (from one another).

It may be that the at least one (ultraviolet) light source is provided (i.e. located) within the (interior of the) photoionisation chamber.

It may be that the at least one (ultraviolet) light source is arranged to direct (i.e. shine) (ultraviolet) light into the (interior of the) photoionisation chamber. For example, it may be that the at least one (ultraviolet) light source is provided (i.e. located) outside the (interior of the) photoionisation chamber, said at least one (ultraviolet) light source being arranged to direct (i.e. shine) (ultraviolet) light into the (interior of the) photoionisation chamber.

The apparatus may further comprise a charged particle detector. The charged particle detector may be provided downstream of the photoionisation chamber.

The apparatus may further comprise electrode current measuring means (e.g. one or more electrode current sensors) configured to measure at least one electrode current flowing to or from at least one electrode (e.g. flowing between at least one pair of electrodes (from said plurality of electrodes)) and detector current measuring means (e.g. one or more detector current sensors) configured to measure a detector current flowing from the charged particle detector.

It may be that the plurality of electrodes comprises at least one first electrode and at least two second electrodes. It may be that the at least one first electrode and the at least two second electrodes are configured to provide (concurrently) a first potential difference between a first electrode (of said at least one first electrodes) and a second electrode (of said at least two second electrodes), and a second potential difference between said first electrode and another second electrode (of said at least two second electrodes).

The first and second potential differences may be the same (as one another). Alternatively, the first and second potential differences may be different (from one another).

It may be that the apparatus comprises a plurality of electrode current measuring means (e.g. a plurality of electrode current sensors), each electrode current measuring means configured to measure an electrode current flowing to or from at least one respective electrode (e.g. between at least one respective pair of first electrode and second electrodes).

It may be that the plurality of electrodes are coupled to the at least one power supply by way of a voltage regulation circuit configured to provide (in use) said at least two concurrent (different) potential differences.

The plurality of electrodes are typically configured such that the respective portions of the photoionisation chamber across which the at least two concurrent potential differences are provided (in use) are non-overlapping portions of the photoionisation chamber. It may be that said respective portions of the photoionisation chamber are contiguous (i.e. abutting) portions of the photoionisation chamber. Said respective portions of the photoionisation chamber are typically arranged along (e.g. spaced out along) a (longitudinal) length of the photoionisation chamber along the gas flow path. The at least two concurrent potential differences are typically applied such that the electric field lines are arranged generally perpendicular to the (longitudinal) length of the photoionisation chamber, i.e. perpendicular to the direction along which gas typically flows through the photoionisation chamber. That is to say, the at least two concurrent potential differences are typically applied such that negatively charged ions and/or photoelectrons and/or positively charged particles initially travelling along the gas flow path are deflected away from said gas flow path by an electromotive force acting in a direction substantially perpendicular to said gas flow path.

It may be that one or more (e.g. each) of the at least two potential differences provided by the plurality of electrodes is individually variable between at least first and second different DC voltages. It may be that each of the at least first and second different DC voltages is a non-alternating voltage.

It may be that the light source is an ultraviolet light source configured to emit ultraviolet light.

A sixth aspect of the invention provides a method of measuring particles (e.g. determining concentration and/or size parameters of particles) in a gas sample, the method comprising: directing the gas sample through a photoionisation chamber; illuminating the gas sample within the photoionisation chamber; concurrently applying two or more (different) (DC) (electric) potential differences, by way of a plurality of electrodes, across (different) respective portions of (an interior of) the photoionisation chamber through which sample gas flows; and measuring one or more electrode currents flowing to or from at least one electrode from the plurality of electrodes (e.g. between respective pairs of the plurality of electrodes).

By applying at least two (different) (DC) potential differences concurrently across at least two different portions of the photoionisation chamber, particles having different sizes and/or masses are typically trapped within different portions of the photoionisation chamber.

Each of the at least two potential differences may be the same (as one another). Alternatively, some or all of the at least two potential differences may be different (from one another).

The method may further comprise the step of: directing sample gas exiting the photoionisation chamber towards a charged particle detector. The method may further comprise the step of: measuring a detector current flowing to or from the charged particle detector.

By comparing the one or more electrode currents and the detector current, the apparatus may be used to determine a size distribution of particles in the gas sample.

It may be that the plurality of electrodes comprises at least one first electrode and at least two second electrodes. It may be that the step of concurrently applying two or more (different) potential differences, by way of the plurality of electrodes, across respective portions of the photoionisation chamber through which sample gas flows further comprises: applying a first potential difference between a first electrode (of the at least one first electrodes) and a second electrode (of the at least two second electrodes) and concurrently applying a second potential difference between said first electrode and another (different) second electrode (of the at least two second electrodes).

The first and second potential differences may be the same (as one another). Alternatively, the first and second potential differences may be different (from one another).

It may be that the step of measuring one or more electrode currents flowing to or from at least one electrode (e.g. between respective pairs of the plurality of electrodes) further comprises: measuring a first electrode current flowing between the first electrode and the second electrode and measuring a second electrode current flowing between said first electrode and said another (different) second electrode.

It may be that the plurality of electrodes are coupled to the at least one power supply by way of a voltage regulation circuit configured to provide (in use) said at least two concurrent (different) potential differences.

It may be that the plurality of electrodes are configured such that the respective portions of the photoionisation chamber across which the at least two concurrent potential differences are provided (in use) are non-overlapping portions of the photoionisation chamber. It may be that the respective portions of the photoionisation chamber are contiguous (i.e. abutting) portions of the photoionisation chamber. Said respective portions of the photoionisation chamber are typically arranged along (e.g. spaced out along) a (longitudinal) length of the photoionisation chamber along the gas flow path.

It may be that the one or more electrode currents are measured by way of electrode current measuring means (e.g. one or more electrode current sensors). It may be that the detector current is measured by way of detector current measuring means.

The method may further comprise the step of: varying one or more of the at least two potential differences provided by the plurality of electrodes between at least first and second different DC voltages. It may be that each of the at least first and second different DC voltages is a non-alternating voltage.

It may be that the step of illuminating the gas sample within the photoionisation chamber comprises illuminating the gas sample with (ultraviolet) light. It may be that the step of illuminating the gas sample within the photoionisation chamber comprises shining (e.g. directing) (ultraviolet) light towards and/or into and/or onto the gas sample (within the photoionisation chamber). It may be that the step of illuminating the gas sample within the photoionisation chamber comprises illuminating the (interior of the) photoionisation chamber The gas sample and/or the (interior of the) photoionisation chamber may be illuminated by a light source (e.g. by an ultraviolet light source). Light (e.g. ultraviolet light) may be directed towards and/or into and/or onto the gas sample from the light source (e.g. from the ultraviolet light source).

It may be that the method steps of the sixth aspect of the invention are performed in any given order.

Seventh and eighth aspects of the invention relate to the problem of capturing airborne particles of matter. Many industrial processes, including combustion, generate airborne particles which create smog and cause negative health effects. Inhalable nanoparticles (particularly particles under 100 nm in diameter) can be particularly harmful as they can penetrate the alveoli of the lungs and be transported into the bloodstream. Several jurisdictions have reacted to scientific evidence by introducing more rigorous emissions standards, e.g. for power plants and cars. There is therefore a need for effective air filtration systems.

Conventional air filtration techniques for fine particles (less than 2500 nm diameter) include membrane or fabric filtration, or controlled precipitation. Membrane or fabric based methods such as HEPA filters are very effective at removing particulate matter, but introduce a high pressure drop as the bulk flow of air is restricted by the filter. Such filters need to be regularly replaced or regenerated. In conventional electrostatic precipitation (ESP), an air stream is not directly acted upon to filter the air, therefore ESP does not create a pressure drop comparable to HEPA filters. However, ESP is not as effective as HEPA filters, is not effective at all for low particle sizes (<50 nm) due to inefficient particle charging by corona discharge methods, requires high voltages (>30 kV), and produces localized ozone which exacerbates respiratory issues. Accordingly, there is a need for improved air filtration methods.

A seventh aspect of the invention provides filtering apparatus comprising an inlet for receiving gas (e.g. a mixture of gas and particles), a photoionisation chamber, at least one light source arranged to illuminate an interior of the photoionisation chamber, first and second electrodes coupled to a power source and configured to provide a DC potential therebetween, and an outlet, together defining a gas flow path from the inlet, through the photoionisation chamber and towards the outlet, the gas flow path passing between the first and second electrodes.

The first and second electrodes may be arranged so as to provide the DC potential across at least a portion of the photoionisation chamber. The first and second electrodes may thereby form a particle and/or ion trap. The gas flow path may therefore be defined from the inlet, through the DC potential (i.e. the particle and/or ion trap) within the photoionisation chamber, and towards the outlet. Some (preferably a majority (e.g. at least 70%, more typically at least 80%, even more typically at least 90%), for example, all) particles passing through the photoionisation chamber between the first and second electrodes may be captured by the particle and/or ion trap, thereby removing (e.g. filtering) said particles from the flow of gas. By arranging the first and second electrodes so as to provide the DC potential across at least a portion of the photoionisation chamber, the likelihood of charged particle and ion recombination is reduced, thereby increasing the extrinsic charging efficiency of the particles and therefore the capture efficiency. Furthermore, the apparatus is made more compact.

Alternatively, the first and second electrodes may be arranged so as to provide the DC potential across at least a portion of (e.g. the entire) the gas flow path (immediately) downstream of the photoionisation chamber. The first and second electrodes may thereby form a particle and/or ion trap downstream of the photoionisation chamber. The gas flow path may therefore be defined from the inlet, through the photoionisation chamber, through the DC potential (i.e. the particle and/or ion trap), and towards the outlet. Some (preferably a majority (e.g. at least 70%, more typically at least 80%, even more typically at least 90%), for example, all) particles exiting the photoionisation chamber and passing between the first and second electrodes may be captured by the particle and/or ion trap, thereby removing (e.g. filtering) said particles from the flow of gas. By providing the first and second electrodes downstream of the photoionisation chamber, the photoionisation chamber is more easily accessible for cleaning or maintenance purposes.

It may be that the at least one (ultraviolet) light source is provided (i.e. located) within the (interior of the) photoionisation chamber.

It may be that the at least one (ultraviolet) light source is arranged to direct (i.e. shine) (ultraviolet) light into the (interior of the) photoionisation chamber. For example, it may be that the at least one (ultraviolet) light source is provided (i.e. located) outside the (interior of the) photoionisation chamber, said at least one (ultraviolet) light source being arranged to direct (i.e. shine) (ultraviolet) light into the (interior of the) photoionisation chamber.

An eighth aspect of the invention provides filtering apparatus comprising an inlet for receiving gas (e.g. a mixture of gas and particles), a photoionisation chamber, at least one light source arranged to illuminate an interior of the photoionisation chamber, a plurality of electrodes coupled to at least one power supply, the plurality of electrodes comprising a first pair of electrodes, configured to provide a first DC potential difference therebetween, and a second pair of electrodes, configured to provide a second DC potential difference therebetween, and an outlet, together defining a gas flow path from the inlet, through the photoionisation chamber and towards the outlet. The gas flow path typically passes between the first pair of electrodes and between the second pair of electrodes.

It may be that the first pair of electrodes is defined by a first electrode and a second electrode. It may be that the gas flow path passes between the first and second electrodes. It may be that the second pair of electrodes is defined by a third electrode and a fourth electrode. It may be that the gas flow path passes between the third and fourth electrodes. However, one electrode (e.g. a common ground) may be common to both the first pair of electrodes and the second pair of electrodes. For example, the first pair of electrodes may comprise a first electrode and a second electrode, and the second pair of electrodes may comprise said first electrode and a third electrode, the gas flow path passing between the first electrode and the second electrode and between the first electrode and the third electrode.

The first pair of electrodes may be arranged so as to provide the first DC potential difference across at least a portion of the photoionisation chamber. The first pair of electrodes may thereby form an ion trap (or a particle and ion trap). The ion trap typically captures gas ions generated on photoionisation of particles in the gas in the photoionisation chamber. By removing (e.g. filtering) said gas ions from the gas flow, efficiency of photoionisation (i.e. charging) of particles in the photoionisation chamber is increased.

The second pair of electrodes may be arranged so as to provide the second DC potential difference across at least a portion of (e.g. the entire) the gas flow path (immediately) downstream of the photoionisation chamber. The second pair of electrodes may thereby form a particle trap (or a particle and ion trap) downstream of the photoionisation chamber. The gas flow path may therefore be defined from the inlet, through the first DC potential difference (i.e. the ion trap) within the photoionisation chamber, through the second DC potential difference (i.e. the particle trap), and towards the outlet. Some (preferably a majority (e.g. at least 70%, more typically at least 80%, even more typically at least 90%), for example, all) particles exiting the photoionisation chamber and passing between the third and fourth electrodes may be captured by the particle trap, thereby removing (filtering) said particles from the flow of gas.

It may be that the first and second pairs of electrodes are coupled to the at least one power supply by way of a voltage regulation circuit configured to provide (in use) said first and second DC potential differences.

The magnitude of the second DC potential difference is typically larger than (e.g. significantly larger than (for example, at least 50% larger than, at least 100% larger than, at least 200% larger than)) the magnitude of the first DC potential difference. Large potential differences are typically required to capture particles than are required to capture gas ions due to the greater mobility of particles relative to gas ions.

It may be that the light source is an ultraviolet light source configured to emit ultraviolet light.

It may be that the at least one (ultraviolet) light source is provided (i.e. located) within the (interior of the) photoionisation chamber.

It may be that the at least one (ultraviolet) light source is arranged to direct (i.e. shine) (ultraviolet) light into the (interior of the) photoionisation chamber. For example, it may be that the at least one (ultraviolet) light source is provided (i.e. located) outside the (interior of the) photoionisation chamber, said at least one (ultraviolet) light source being arranged to direct (i.e. shine) (ultraviolet) light into the (interior of the) photoionisation chamber.

Optional features of any one aspect of the invention are, mutatis mutandis, optional features of any other aspect of the invention.

DESCRIPTION OF THE DRAWINGS

An example embodiment of the present invention will now be illustrated with reference to the following Figures in which.

DETAILED DESCRIPTION OF EXAMPLE EMBODIMENTS

First Example Embodiment of the Invention

Figure 1:
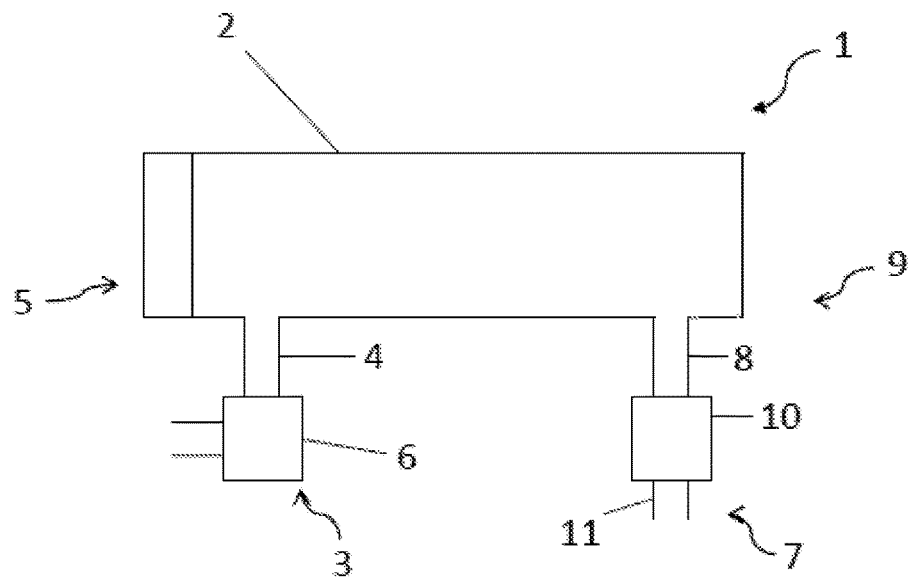
FIG. 1 is a plan view of a particle sensor of the first and second example embodiments of the invention.
Figure 2:
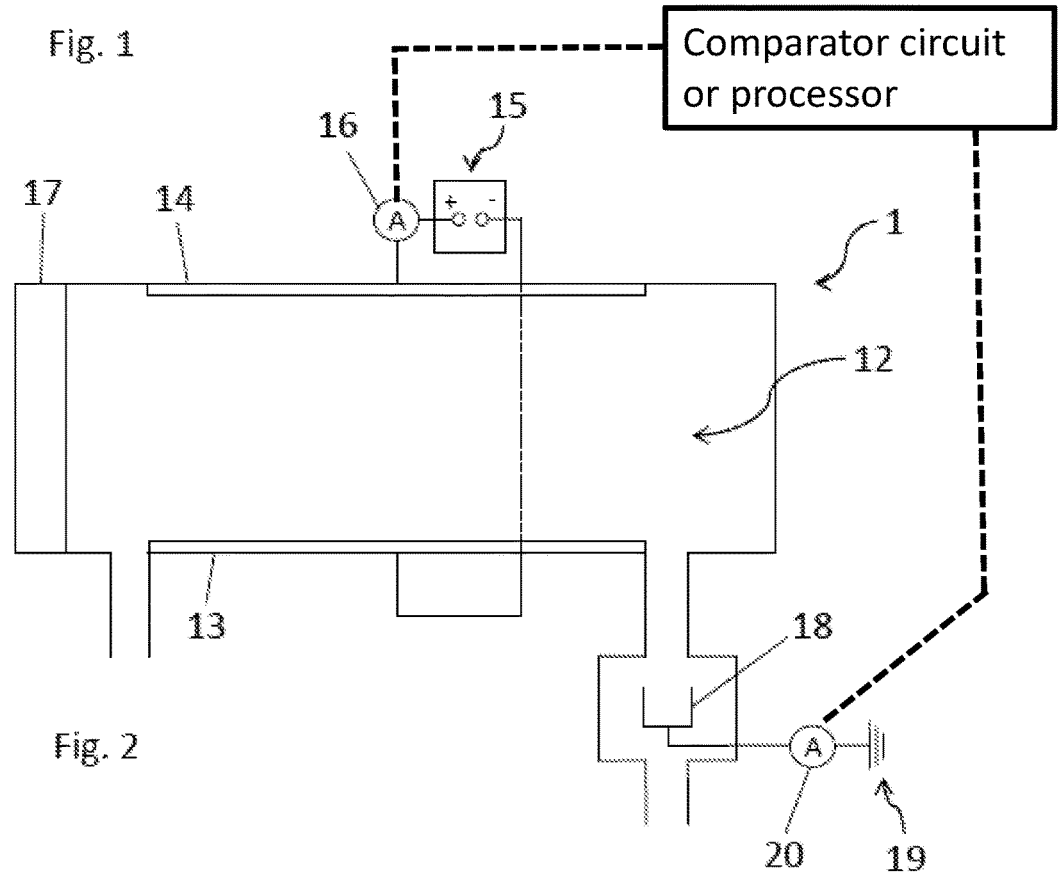
FIG. 2 is a schematic cross sectional view of the particle sensor of FIG. 1.

In a first example embodiment, as illustrated in FIGS. 1 and 2, a particle sensor 1 comprises a sensor body 2 made of aluminium. A sample gas inlet 3 comprises an inlet passageway 4 which extends into the body towards a first end 5. A pump 6 is coupled to the inlet passageway 4 and is configured to pump sample gas into the sensor body through the inlet passageway. A sample gas outlet 7 comprises an outlet passageway 8 which extends out of the body towards a second end 9 opposite said first end 5. The outlet passageway 8 connects the sensor body to a collector chamber 10. A second outlet passageway 11 extends away from the collector chamber 10.

The interior of the sensor body 2 is hollow. The interior of the sensor body 2 forms an elongate photoionisation chamber 12 (see FIG. 2). A first planar electrode 13, made of stainless steel, is provided on a first internal surface of the photoionisation chamber 12 extending between the inlet 3 and the outlet 7. A second planar electrode 14, also made of stainless steel, is provided on a second internal surface of the photoionisation chamber 12 extending between the inlet 3 and the outlet 7, opposite the first electrode 13. The first and second electrodes 13,14 are both connected to an earthed DC power supply 15 in series with an ammeter 16. The first electrode 13 is connected to the negative terminal of the power supply 15. The second electrode 14 is connected to the positive terminal of the power supply 15.

A photoionisation lamp 17 is provided at the first end of the sensor body. The photoionisation lamp 17 is coupled to a power supply (not shown). The photoionisation lamp is configured to emit, in use, ultraviolet light having wavelengths within the range 150 nm-260 nm. The photoionisation lamp is oriented such that emitted ultraviolet light illuminates the entirety of the photoionisation chamber 12.

A Faraday cup electrometer 18 as is generally known in the field of particle detectors is mounted in the collector chamber 10. The Faraday cup electrometer 18 typically consists of an electrically conductive filter (not shown) mounted within a wire mesh (not shown). The Faraday cup electrometer 18 is positioned within the collector chamber 10 such that flow of gas from the photoionisation chamber 12 and into the collector chamber 10 passes through the Faraday cup electrometer 18. In use, any charged particles exiting the photoionisation chamber 12 through the outlet 7 are incident on the Faraday cup electrometer 18. An electrical outlet of the Faraday cup electrometer is connected to earth 19 in series with an ammeter 20.

In use, a gas sample for analysis is pumped into the sensor through the inlet by the pump. Sample gas consequently flows sequentially through the inlet passageway, into and through the photoionisation chamber from the first end towards the second end, and through the outlet passageway to the outlet. The pump is configured to pump the gas sample through the sensor at a known, generally constant gas flow rate.

The power supply connected to the photoionisation lamp 17 is switched on such that the lamp illuminates the photoionisation chamber 12 with ultraviolet light. The gas sample generally comprises a mixture of gaseous atoms and/or molecules and particles suspended in the gas. The gas molecules and/or atoms, as well as the particles, are typically uncharged (i.e. electrically neutral). As the gas sample flows through the photoionisation chamber, particles in the gas sample absorb one or more photons of ultraviolet light emitted by the photoionisation lamp. The wavelength of the ultraviolet light is selected such that absorption of a photon by a particle causes that particle to emit a photoelectron. The wavelength of ultraviolet light emitted by the photoionisation lamp is therefore below a threshold wavelength for particle photoionisation (that is to say, each photon emitted by the photoionisation lamp has an energy above a threshold energy required for particle photoionisation). Absorption of a photon and consequent emission of an electron causes a particle to acquire a net positive charge. Each electron which is emitted by a particle on photoionisation generally proceeds to ionise a nearby gas atom or molecule, thereby forming a negatively charged gas ion. Photoionisation of the particles in the gas sample takes place between the first and second electrodes 13,14.

When the power supply 15 connected to the electrodes 13,14 is switched off, after a characteristic period of time (dependent on, inter alia, the concentration of particles in the gas), negatively charged gas ions and positively charged particles in the gas sample in the photoionisation chamber 12 are attracted to one another and tend to come into contact with one another, resulting in the transfer of electrons back from the ions to the particles, thereby neutralising both charges in a process called recombination. Consequently, only a portion of the particles in the gas sample exiting the photoionisation chamber 12 at the second end 9 and flowing over the Faraday cup electrometer 18 in the collector chamber 10 are electrically charged. While a collector signal measured by the ammeter 20 is detectable, the strength of the signal is typically only partially correlated to the number and size of the particles in the gas sample. Therefore, the sensitivity of the particle detector 1, when the power supply 15 is switched off, is relatively poor.

However, when the power supply 15 connected to the electrodes 13,14 is switched on, a substantially uniform DC potential difference V is provided across the photoionisation chamber between the first and second electrodes 13,14. The applied potential difference V typically generates an electric field of between around 1 V/cm to around 100 V/cm across the photoionisation chamber. This mode is illustrated schematically in FIG. 3. Photoionisation of the particles in the gas sample takes place in the electric field between the first and second electrodes 13,14. In this mode, negatively charged gas ions 21 formed on photoionisation of particles in the gas sample are less likely to recombine with positively charged particles 22. The electric field provided between the first and second electrodes exerts a force on the negatively charged ions 21, causing these ions to drift away from the particles towards the second electrode 14 (which functions as an anode) as they flow through the photoionisation chamber 12. In addition, any free photoelectrons which have not combined with gas atoms or molecules to form gas ions will also drift toward the second electrode 14 under the action of the electric field. The electric field also exerts a force on the positively charged particles 22, causing these particles to drift towards the first electrode 13 (which functions as the cathode) as they flow though the photoionisation chamber 12. Nevertheless, because the negatively charged gas ions 21 and any free electrons are relatively more mobile, only the ions and electrons tend to reach the second electrode 14, thereby generating an electrode current which is measured by the ammeter 16. The ions and the free electrons are thus at least partially removed from the flow of gas through the photoionisation chamber 12. The first and second electrodes 13,14 function as an ion trap embedded within the photoionisation chamber.

In contrast, because the positively charged particles 22 are significantly less mobile than the gas ions, the charged particles 22 tend to flow through the photoionisation chamber 12 and through the outlet without being captured by the ion trap. If the photoionisation of particles in the gas sample within the photoionisation chamber 12 is sufficiently high for detectability, the flux of charged particles onto the Faraday cup electrometer 18, and thus the collector signal measured by the ammeter 20, is proportional to a combined parameter $N^{\alpha}D^{\beta}$, in some instances proportional to a measurement of the total effective particle surface area in the gas sample, where N is the concentration of particles in the gas and D is the average particle diameter. The sensor may therefore be calibrated in order to provide a measurement of this total effective particle surface area. The total effective particle surface area measured by the sensor in this mode is more accurate than that detected when no potential difference is applied between the first and second electrodes 13,14.

In this first example embodiment, the measured anode current and the measured collector current are both typically dependent on the total effective particle surface area. The gas sensor may therefore be calibrated to output a total effective particle surface area based on measurement of either the electrode current or the collector current.

Second Example Embodiment of the Invention

In a second embodiment of the invention, the output of the DC power supply 15 in FIG. 2 is varied in use so as to vary the DC potential difference provided between the first and second electrodes 13,14 between a first voltage $V_1$ and a second, larger voltage $V_2$ having the same polarity as $V_1$.

Figure 3:
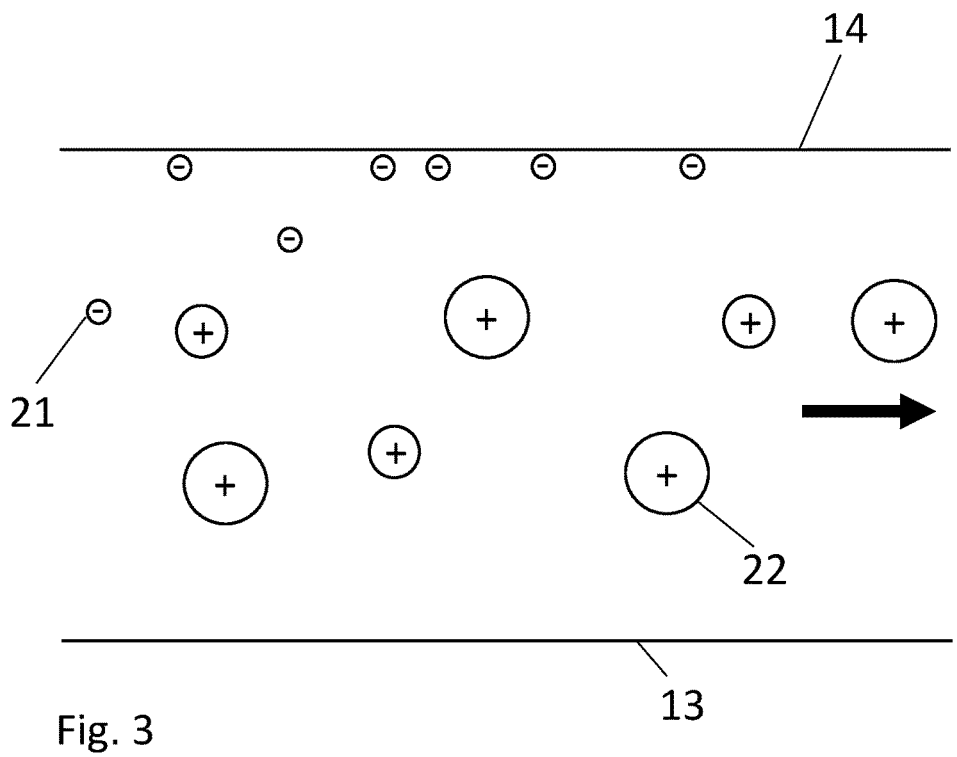
FIG. 3 is a schematic illustration of negatively charged gas ions being trapped by an ion trap of the particle sensor of FIGS. 1 and 2.

When the first voltage $V_1$ is applied between the first and second electrodes 13,14, the sensor operates in essentially the same mode as outlined above for the first embodiment of the invention and as illustrated in FIG. 3. Negatively charged gas ions 21 and free photoelectrons generated by photoionisation of sample gas in the photoionisation chamber 12 drift towards the second electrode 14 and are captured by the ion trap. Positively charged particles 22 are not captured by the ion trap and instead exit the photoionisation chamber through the outlet 7, being collected by the Faraday cup electrometer 18. Both an electrode current measured by the ammeter 16 connected between the first and second electrodes and a collector current measured by the ammeter 20 connected to the Faraday cup electrometer are indicative of a total effective surface area of particles in the gas sample.

Figure 4:
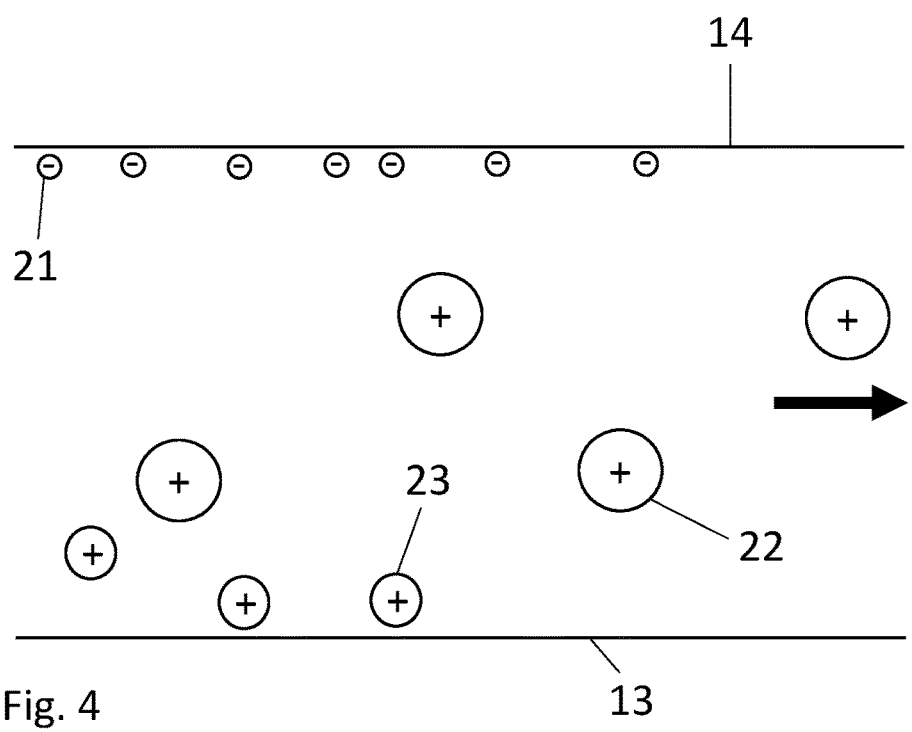
FIG. 4 is a schematic illustration of negatively charged gas ions and positively charged particles being trapped by an ion trap of the particle sensor of FIGS. 1 and 2.

When the potential difference between the first and second electrodes 13,14 is increased to voltage $V_2$, however, the force exerted on the negatively charged gas ions 21, the free electrons and the positively charged particles 22 in the gas sample flowing through the photoionisation chamber 12 is increased. This typically results in a greater proportion of the negatively charged gas ions 21 and free electrons being trapped by the second electrode 14, resulting in both an increased electrode current. Additionally, as illustrated schematically in FIG. 4, some of the positively charged particles 22 may also now drift towards and reach the first electrode 13, thereby further contributing to the electrode current. Smaller, less massive negatively charged particles 23 are most likely to be captured by the ion trap and to contribute to an increased electrode current. Consequently, fewer charged particles 22 exit the photoionisation chamber 12 and are incident on the Faraday cup electrometer 18, resulting in a decreased collector current measured by the ammeter 20. The electrode and detector currents depend sensitively and non-linearly on the magnitude of the applied potential difference.

For a given applied voltage between the first and second electrodes 13,14 and a given flow rate of sample gas through the photoionisation chamber 12, the dependence of the electrode current on the particle concentration N and the mean particle diameter D can be modelled according to $$I_e = a_e N^{\alpha_e} D^{\beta_e}. \quad (1)$$

The inventors have found that dimensionless parameters $\alpha_e$ and $\beta_e$ are functions of the magnitude of the applied potential difference and typically take values between 0.5 and 3.

Similarly, the dependence of the collector current on the particle concentration N and the mean particle diameter D can be modelled according to $$I_c = a_c N^{\alpha_c} D^{\beta_c}. \quad (2)$$

Again, the inventors have found that dimensionless parameters $\alpha_c$ and $\beta_c$ are functions of the magnitude of the applied potential difference and typically take values between 0.5 and 3.

Accordingly, by measuring both the electrode current and the collector current at a first applied voltage $V_1$ and at a second applied voltage $V_2$, equations (1) and (2) may be solved simultaneously to determine both N and D. Consequently, both the particle concentration and the mean particle diameter may both be determined independent of one another from one set of measurements, providing more detailed information about the particles in the gas sample than can be determined using only the first embodiment of the invention.

In a variation of the second example embodiment of the invention, the potential difference applied between the first and second electrodes is varied between a plurality of different voltages (for example, the potential difference may be varied between 10 different voltages). For each additional voltage, the electrode and the collector currents change, thereby providing two more equations (1) and (2) which may be solved to determine N and D. The inventors have therefore found that by increasing the number of different voltages applied sequentially across the photoionisation chamber, the accuracy to which the particle concentration and mean particle diameter may be determined is increased.

Third Example Embodiment of the Invention

Figure 5:
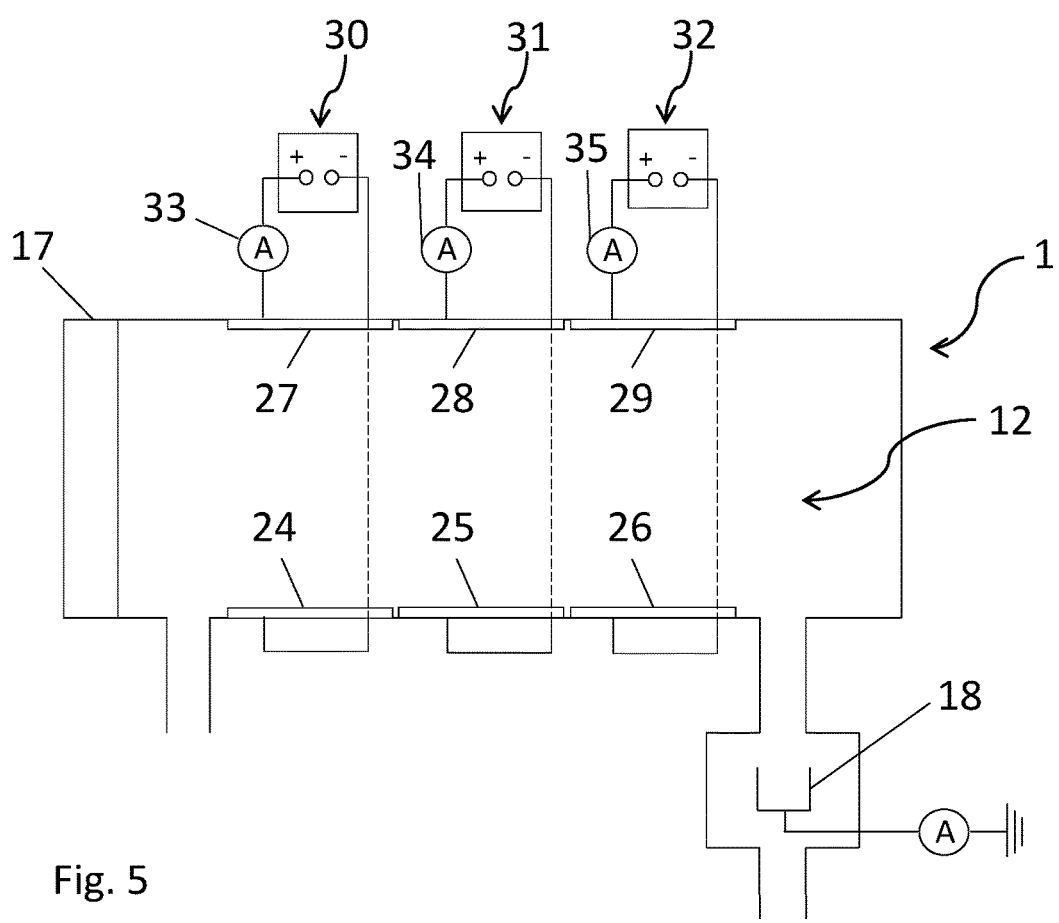
FIG. 5 is a schematic cross sectional view of a particle sensor of the third example embodiment of the invention.

In a third embodiment of the invention, as illustrated in FIG. 5, first, second and third cathodes 24,25,26 are provided along a first side of the photoionisation chamber 12 of the particle detector 1. First, second and third anodes 27,28, 29 are provided along a second side of the photoionisation chamber 12, opposite said first, second and third cathodes respectively. Each cathode-anode pair is electrically connected to one another via a respective variable DC power supply 30,31,32 in series with a corresponding ammeter 33,34,35. The variable power supplies 30,31,32 are configured to provide DC potential difference $V_3$ between the first cathode 24 and the first anode 27, DC potential difference $V_4$ between the second cathode 25 and the second anode 28, and DC potential difference $V_5$ between the third cathode 26 and the third anode 29. $V_3$, $V_4$ and $V_5$ each have the same polarity; $V_4$ is larger than $V_3$, and $V_5$ is larger than $V_4$.

In use, a gas sample is pumped by the pump through the inlet 6, into and through the photoionisation chamber 12, and out through the outlet 7. Particles in the gas sample are photoionised by ultraviolet light emitted by the photoionisation lamp 17, thereby forming positively charged particles and negatively charged gas ions. As the particles and ions flow through the photoionisation chamber 12, they are deflected away from a general flow direction by the applied potential differences. As the gas flows between the first cathode-anode pair, all of the gas ions are trapped by the first anode 27. In this region, the potential difference $V_3$ is however not strong enough to trap any of the positively charged particles. As the positively charged particles subsequently flow through the stronger potential difference $V_4$ provided between the second cathode-anode pair, some of the smaller charged particles are trapped by the second cathode 25. Additionally, as the remaining positively charged particles subsequently flow through the even stronger potential difference $V_5$ provided between the third cathode-cathode pair, even more of the smaller particles and some of the larger particles are trapped by the third cathode 26. Any remaining positively charged particles in the gas flow not trapped by any of the three electrode pairs flow out of the photoionisation chamber 12 and are detected by the Faraday cup electrometer 18.

Accordingly, four currents are measured: three electrode currents corresponding to the current flowing between each of the three anode-cathode pairs and one detector current. Each of these four currents may be related to the particle concentration and mean particle diameter in the gas sample according to the following equations:

$$I_{e1} = a_{e1} N^{\alpha_{e1}} D^{\beta_{e1}}, \quad (3)$$

$$I_{e1} = a_{e2} N^{\alpha_{e2}} D^{\beta_{e2}}, \quad (4)$$

$$I_{e3} = a_{e3} N^{\alpha_{e3}} D^{\beta_{e3}}, \quad (5)$$

and $$I_c = a_c N^{\alpha_c} D^{\beta_c}, \quad (6)$$

where the subscripts e1, e2 and e3 indicate each of the first, second and third electrode pairs respectively. By measuring the three electrode currents and one detector current, the concentration and mean diameter of particles trapped by each electrode pair or escaping from the photoionisation chamber to the detector can be determined simultaneously. A particle size distribution of particles in the gas sample may therefore be determined.

Fourth Example Embodiment of the Invention

Figure 6:
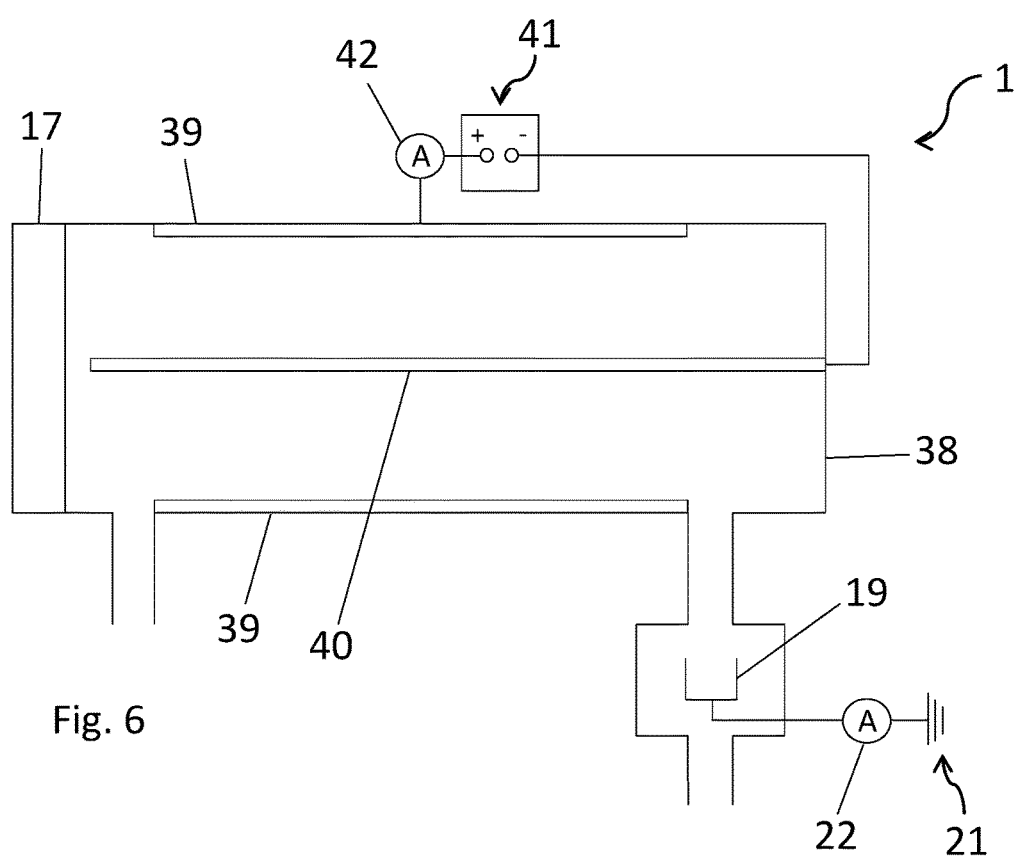
FIG. 6 is a schematic cross sectional view of a particle sensor of the fourth example embodiment of the invention.

In a fourth example embodiment of the invention, as illustrated in FIG. 6, the sensor body 2 of the first and second example embodiments of the invention is replaced by a substantially cylindrical sensor body 38. The cylindrical sensor body 38 is positioned with respect to the inlet 3 and the outlet 7 such that gas flows substantially parallel to the longitudinal axis of the cylindrical body as it travels from the inlet to the outlet. A substantially cylindrical first electrode 39 is provided on an internal surface of the cylindrical sensory body 38. The cylindrical first electrode 39 extends between the inlet and the outlet, around the internal circumference of the cylindrical sensor body 38. A second, axial electrode 40 is provided within the cylindrical sensor body, aligned along the longitudinal axis, spaced apart from the first electrode 39. The axial electrode is mounted to the sensor body at the second end 9. The first and second electrodes 39 and 40 are connected to a variable DC power supply 41 in series with an ammeter 42. The first electrode 39 is connected to the positive terminal of the power supply 41, the second electrode is connected to the negative terminal of the power supply 41. In use, a variable DC potential difference may be applied across the photoionisation chamber between the first cylindrical electrode 39 and the second axial electrode 40. The sensor of this fourth example embodiment of the invention may be used in any of the modes described with regard to the first and second example embodiments of the invention.

Fifth Example Embodiment of the Invention

Figure 7:
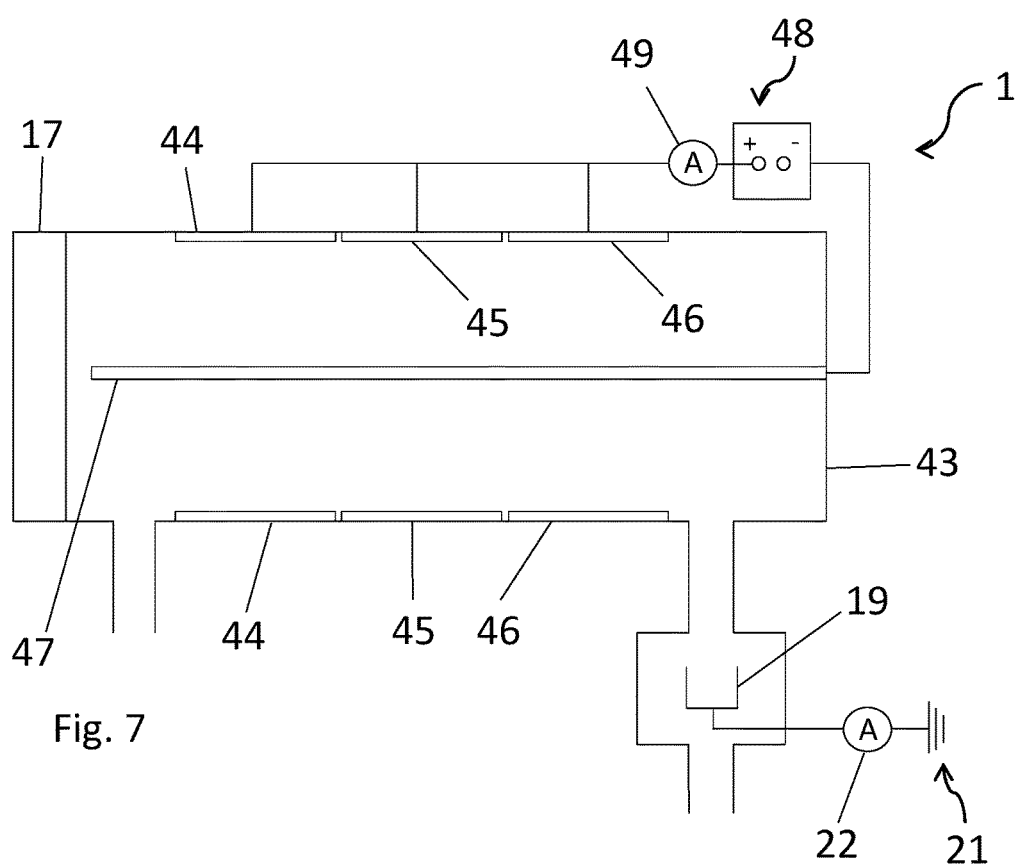
FIG. 7 is a schematic cross sectional view of a particle sensor of the fifth example embodiment of the invention.

In a fifth example embodiment of the invention, as illustrated in FIG. 7, the sensor body 2 of the third example embodiment of the invention is replaced by a substantially cylindrical sensor body 47. The cylindrical sensor body 47 is positioned with respect to the inlet 3 and the outlet 7 such that gas flows substantially parallel to the longitudinal axis of the cylindrical body as it travels from the inlet to the outlet. Three substantially cylindrical first electrodes 44,45, 46 are provided along an internal surface of the cylindrical sensory body 38, spaced apart from one another. Each cylindrical first electrode 44,45,46 extends around the internal circumference of the cylindrical sensor body 38. A second, axial electrode 47 is provided within the cylindrical sensor body, aligned along the longitudinal axis, spaced apart from the first electrodes 44,45,46. The axial electrode 47 is mounted to the sensor body at the second end 9. The first and second electrodes 44,45,46,47 are connected to a variable DC power supply 48 in series with an ammeter 49. The first electrodes 44,45,46 are connected to the positive terminal of the power supply 48, while the second electrode 47 is connected to the negative terminal of the power supply 48. In use, a variable DC potential difference may be applied across the photoionisation chamber between the first cylindrical electrodes 44, 45,46 and the second axial electrode 47. The sensor of this fourth example embodiment of the invention may be used as is described with regard to the third example embodiments of the invention. Additionally, a voltage regulation circuit (not shown) may be provided between the power supply 48 and the first electrodes 44,45, 46, in order to individually select the potential difference between each electrode pair 44,47 and 45,47 and 46,47. Alternatively, each first electrode 44,45,46 may be connected to the second electrode 47 by way of an individual power supply in series with an individual ammeter, such that each potential difference may be varied individually.

Further variations and modifications may be made within the scope of the invention herein disclosed.

The pump need not be coupled to the inlet passageway as is shown in FIG. 1. The pump may instead be positioned at any suitable location in the device in order to generate flow of sample gas through the photoionisation chamber. For example, an extraction pump may be provided towards the second end of the sensor body. Alternatively, the pump may be replaced by any other component capable of driving flow of sample gas through the photoionisation chamber, such as a fan.

Sixth Example Embodiment of the Invention

Figure 18:
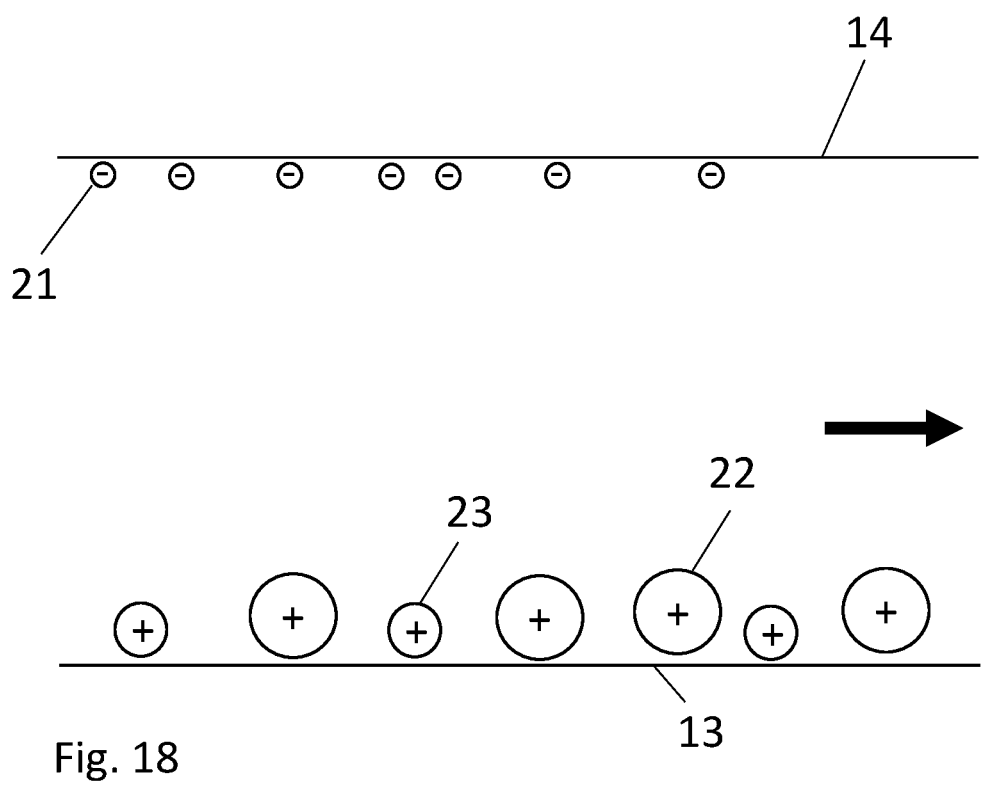
FIG. 18 is a schematic illustration of negatively charged gas ions being trapped by an ion or particle trap of the particle sensor of FIG. 2 or particle sensor or air filter of FIG. 19.

In a sixth example embodiment of the invention, when the output of the DC power supply 15 in FIG. 2 connected to the electrodes 13,14 is switched on, a substantially uniform DC potential difference V is provided across the photoionisation chamber between the first and second electrodes 13,14. The applied potential difference V typically generates an electric field of between around 100 V/cm to around 10000 V/cm across the photoionisation chamber. This mode is illustrated schematically in FIG. 18. Photoionisation of the particles in the gas sample takes place in the electric field between the first and second electrodes 13,14. In this mode, negatively charged gas ions 21 formed on photoionisation of particles in the gas sample are less likely to recombine with positively charged particles 22, 23. The electric field provided between the first and second electrodes exerts a force on the negatively charged ions 21, causing these ions to drift away from the particles towards the second electrode 14 (which functions as an anode) as they flow through the photoionisation chamber 12. In addition, any free photoelectrons which have not combined with gas atoms or molecules to form gas ions will also drift toward the second electrode 14 under the action of the electric field. The electric field also exerts a force on the positively charged particles 22, 23, causing these particles to drift towards the first electrode 13 (which functions as the cathode) as they flow though the photoionisation chamber 12. Because the electric field strength is high enough, the negatively charged gas ions 21 and any free electrons tend to reach the second electrode 14 and the positively charged particles 22, 23 tend to reach the first electrode 13 to be captured, thereby both generating an electrode current which is measured by the ammeter 16, as well as acting as an airborne particle filter by removing particles from the gas flow. The ions, free electrons, and particles are thus at least partially removed and more likely substantially or fully removed from the flow of gas through the photoionisation chamber 12. The first and second electrodes 13,14 function as an ion and particle trap embedded within the photoionisation chamber.

Seventh Example Embodiment of the Invention

Figure 19:
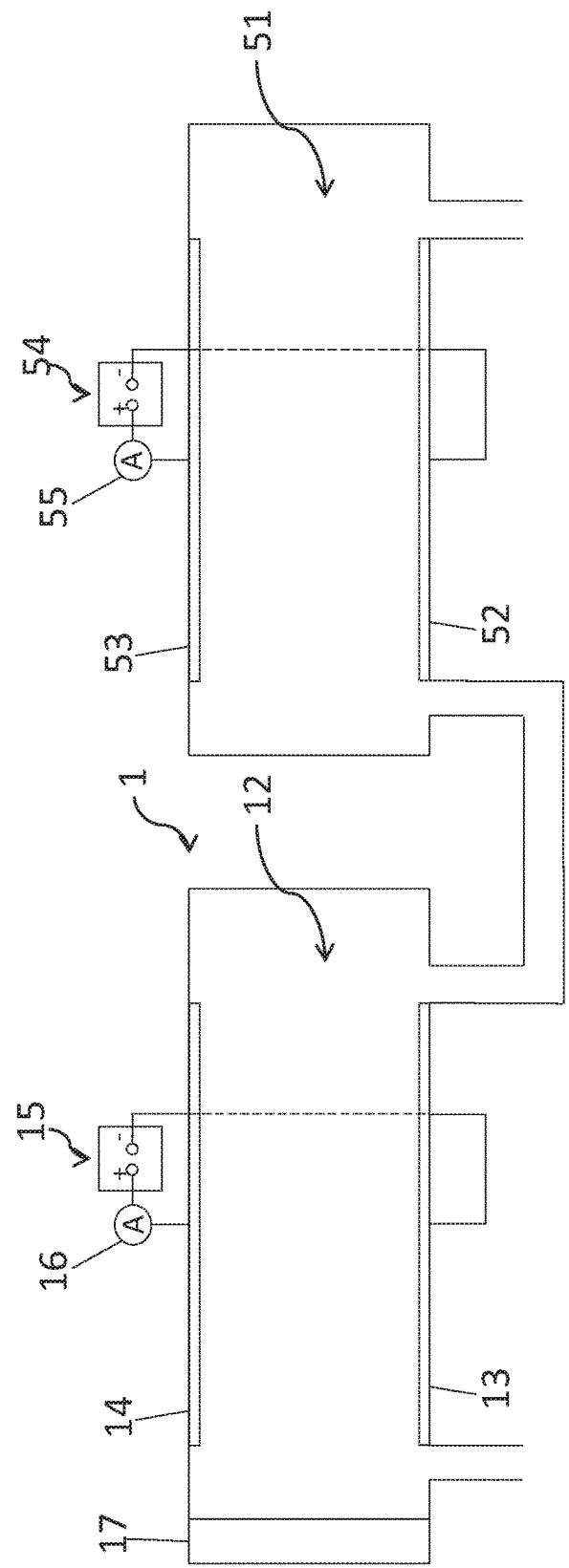
FIG. 19 is a schematic cross sectional view of a particle sensor or air filter of the seventh example embodiment of the invention.

In a seventh example embodiment of the invention, when the output of the DC power supply 15 in FIG. 19 connected to the electrodes 13,14 is switched on, a substantially uniform DC potential difference V is provided across the photoionisation chamber between the first and second electrodes 13,14. The applied potential difference V typically generates an electric field of between around 1 V/cm to around 100 V/cm across the photoionisation chamber. This mode is illustrated schematically in FIG. 3. Photoionisation of the particles in the gas sample takes place in the electric field between the first and second electrodes 13,14. In this mode, negatively charged gas ions 21 formed on photoionisation of particles in the gas sample are less likely to recombine with positively charged particles 22, 23. The electric field provided between the first and second electrodes exerts a force on the negatively charged ions 21, causing these ions to drift away from the particles towards the second electrode 14 (which functions as an anode) as they flow through the photoionisation chamber 12. In addition, any free photoelectrons which have not combined with gas atoms or molecules to form gas ions will also drift toward the second electrode 14 under the action of the electric field. The electric field also exerts a force on the positively charged particles 22, 23, causing these particles to drift towards the first electrode 13 (which functions as the cathode) as they flow though the photoionisation chamber 12. Nevertheless, because the negatively charged gas ions 21 and any free electrons are relatively more mobile, only the ions and electrons tend to reach the second electrode 14, thereby generating an electrode current which is measured by the ammeter 16. The ions and the free electrons are thus at least partially removed from the flow of gas through the photoionisation chamber 12 reducing the likelihood of recombination between charged particles 22, 23 and charged gas ions 21, and thereby increasing the extrinsic charging efficiency of particles. Because the positively charged particles 22, 23 are significantly less mobile than the gas ions, the charged particles 22, 23 tend to flow through the photoionisation chamber 12 and through a tube 50 to a capture chamber 51 in which a high DC potential difference is applied.

When the output of the DC power supply 54 in FIG. 19 connected to the electrodes 52,53 is switched on, a substantially uniform DC potential difference V is provided across the photoionisation chamber between the third and fourth electrodes 52,53. The applied potential difference typically generates an electric field of between around 100 V/cm to around 10000 V/cm across the capture chamber. This mode is illustrated schematically in FIG. 18. Because the electric field strength is high enough, any remaining negatively charged gas ions 21 and any free electrons tend to reach the fourth electrode 53 and the positively charged particles 22, 23 tend to reach the third electrode 52 to be captured, thereby both generating an electrode current which is measured by the ammeter 55, as well as acting as a sensor or as an airborne particle filter by removing particles from the gas flow.

Experimental results

Experimental results achieved using a sensor of the type illustrated schematically in FIG. 7 are shown in FIGS. 8 to 15. The experimental setup was as follows. A photoionisation chamber 210 mm in length, 50 mm in external diameter, and 30 mm in internal diameter, and made of electrically insulating PTFE, enclosed three adjacent aluminium cylinders (functioning together as the first electrode) of 65 mm in length, 30 mm in external diameter, and 25 mm in internal diameter, separated by PTFE spacers of 5 mm in length, 30 mm in external diameter, and 25 mm in internal diameter. A concentrically located stainless steel rod (functioning as the second electrode) of 210 mm in length and 1.5 mm in diameter was mounted at the end of the photoionisation chamber nearest the outlet, extending co-axially along the entire length of the photoionisation chamber. A 3 W UV lamp (Dinies Technologies GmbH, Germany, Model Mini3W52ozon) emitting light of wavelength 185 nm was mounted at the end of the photoionisation chamber nearest the inlet in order to illuminate the photoionisation chamber through a UV-extended fused silica optical window of 25 mm in diameter and 3 mm in thickness. A Keithley electrometer (Keithley Instruments Inc., Cleveland, Ohio, USA, Model 5617B) was connected in series with the first and second electrodes and a variable power supply. The electrometer had an accuracy of ±3 fA. The photoionisation chamber was enclosed in an electrically isolated, aluminium box acting as a Faraday cage, grounded with the electrometer triaxial measurement cable. Flow from the photoionisation chamber was also sampled by an aerosol electrometer (TSI Inc., Shoreview, Minn., USA: Model 3068B) (functioning as the collector) with an accuracy better than 1 fA.

The particle size and concentration were measured by aerosol characterization instrumentation. The number-weighted particle mobility diameter distribution was measured in parallel with the photoionization chamber for aerosol characterization using a Scanning Mobility Particle Sizer (SMPS; TSI Inc.: 3080 Electrostatic Classier, 3081 Differential Mobility Analyzer [DMA], 3025 Condensation Particle Counter [CPC]). The number-weighted mobility diameter distribution gives a measure of mean particle size and total concentration of aerosol particles.

A sample flow of carbonaceous soot particles was produced by flows of propane (65-105 std. cm$^3$/min), air (1.2 std. L/min), and $N_2$ (3 std. L/min) in a co-flow inverse diffusion flame. An ejector diluter with filtered compressed air was used to provide a vacuum to draw the sample gas into the photoionisation chamber. The concentration of particles in the gas flow was varied by changing a diameter of a critical orifice (for example, 0.635 mm) and the flow rate of dilution air. The particle size was varied by changing the flow rate of propane into the flame (higher flow rates yielding larger particle sizes). Stainless steel and conductive silicon tubing were used to minimize particle losses in the sampling lines. Semivolatile organic carbon was removed from the sample gas using a catalytic stripper operated with an internal gas temperature of 350° C. An electrostatic precipitator operated at 3 kV was used to capture particles having any residual charge from the combustion process before they entered the photoionisation chamber and aerosol characterization equipment. The orifice diameter, the flow rate and the voltage state were held constant after any change in each said parameter until a steady state reading could be measured by both the photoionization instrumentation (Keithley and TSI Aerosol Electrometers) and the aerosol characterization instrumentation, taking up to 5 minutes per measurement.

Figure 8:
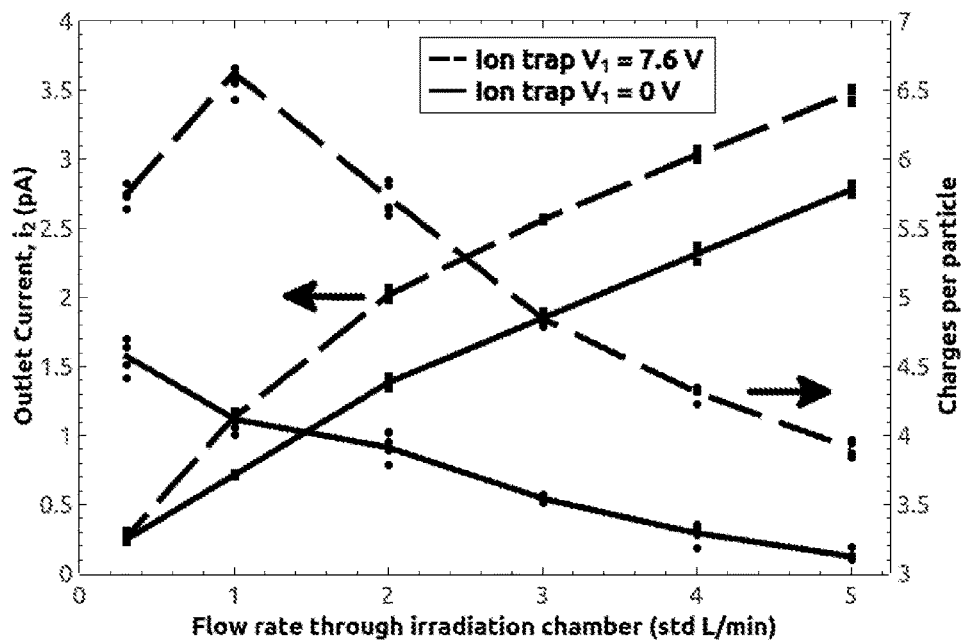
FIG. 8 is a graph of collector current and average charge per particle as a function of gas sample flow rate through the photoionisation chamber of an experimental sensor similar to the fourth example embodiment of the invention.

FIG. 8 shows the total current measured, using the above experimental setup, at the collector (indicated by squares), as well as the average charge per particle (indicated by circles) calculated by dividing the total current by the known total concentration of particles and flow rate, as a function of the gas sample flow rate through the photoionisation chamber at zero applied potential difference (solid lines) and at an applied potential difference of 7.6 V between the first and second electrodes (dashed lines). It can be seen that application of the potential difference causes both the total collector current and the average charge per particle to increase. This indicates that the applied potential difference functions as an ion trap, trapping negatively charged gas ions and reducing ion-particle recombination. It can also be seen that the average charge per particle decreases with increasing flow rate. This is because at higher flow rates there is less time for particle photoionisation to occur. Nevertheless, the total current continues to increase with increasing flow rate because more charged particles pass through the photoionisation chamber, more than compensating for the reduced time for photoionisation. The maximum number of charged particles occurs at a flow rate of 1 std L/min, corresponding to a particle residence time within the photoionisation chamber of 6.2 s.

Figure 9:
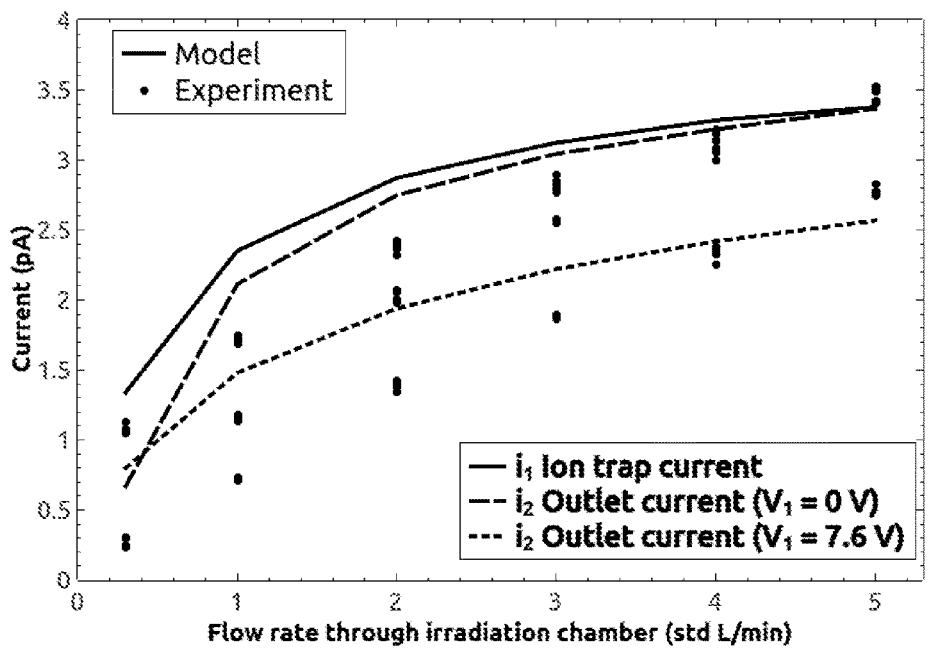
FIG. 9 is a graph of collector current and electrode current as a function of gas sample flow rate through the photoionisation chamber of the experimental sensor of FIG. 8.

FIG. 9 compares the same data for collector current as seen in FIG. 8 with the corresponding electrode current (i.e. the ion trap current) measured at the same time. The flow-rate dependence of the electrode current is similar to that of the collector current. However, the electrode current is consistently higher than the collector current. The inventors believe this is due to loss of charged particles on collision with tube walls between the ion trap and the collector, reducing the number of charged particles reaching the collector.

Figure 10:
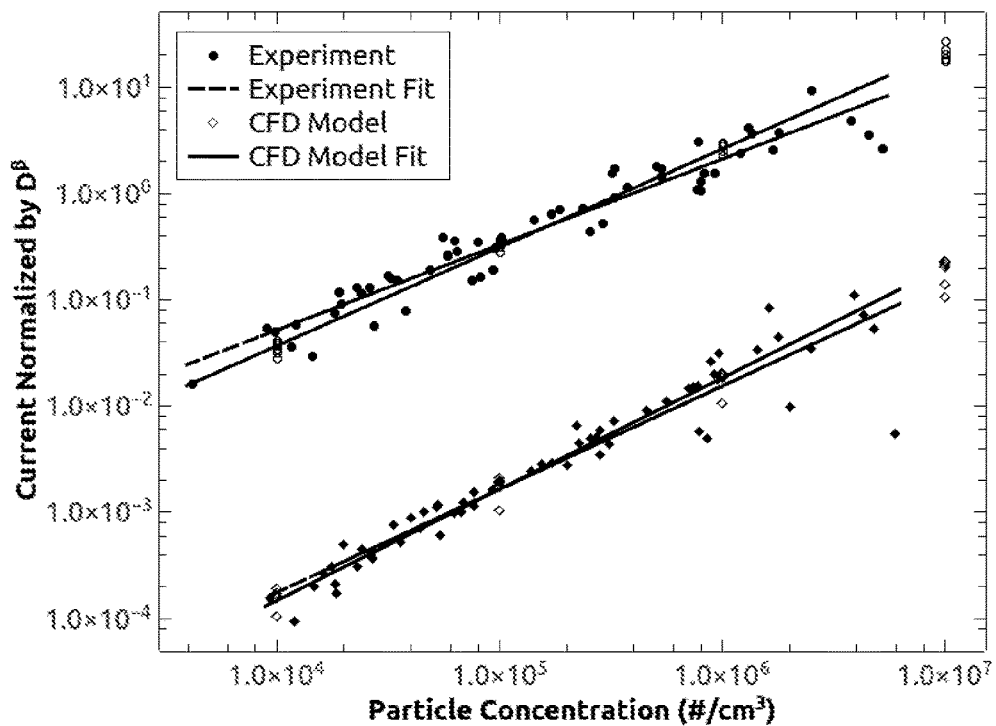
FIG. 10 is a graph of collector current, normalised with respect to particle diameter, as a function of particle concentration in the experimental sensor of FIG. 8.
Figure 11:
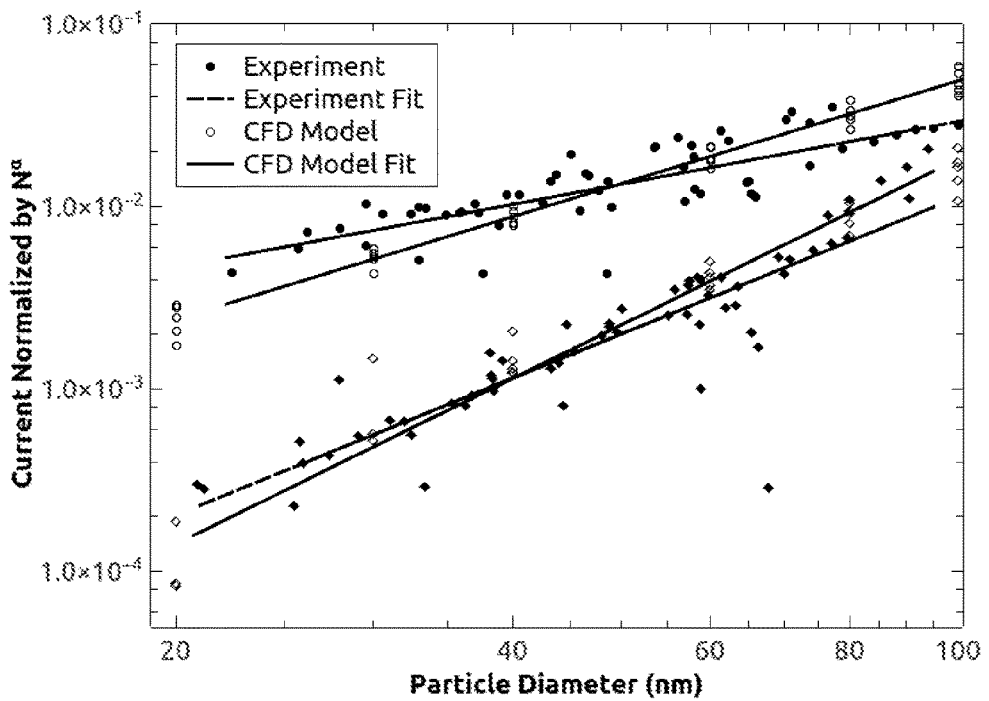
FIG. 11 is a graph of collector current, normalised with respect to particle concentration, as a function of particle diameter in the experimental sensor of FIG. 8.

FIGS. 10 and 11 show how the collector current varies as a function of both particle concentration and particle diameter, and how this behaviour is a function of the potential difference applied between the first and second electrodes. In general, the collector current depends on both the particle concentration N and diameter D according to:

$$I_c = a_c N^{\alpha_c} D^{\beta_c}. \tag{7}$$

Accordingly, FIG. 10 shows the collector current normalised by $D^{\beta_c}$ and plotted on a logarithmic scale as a function of particle concentration for two different applied voltages (the upper data set corresponds to an applied voltage of 7.6 V, while the lower data set corresponds to an applied voltage of 85 V). The concentration exponent $\alpha_c$ is determined from each data set by linear regression. Similarly, FIG. 11 shows the collector current normalised by $N^{\alpha_c}$ and plotted on a logarithmic scale as a function of particle concentration for two different applied voltages (the upper data set corresponds to an applied voltage of 7.6 V, while the lower data set corresponds to an applied voltage of 85 V). The concentration exponent $\beta_c$ is again determined from each data set by linear regression. The inventors believe that the higher voltage measurements show a decreased collector current because more mobile charged particles (i.e. the smaller charged particles) are captured by the ion trap at these voltages (and potentially also because of increased photoemission from housing walls).

Figure 12:
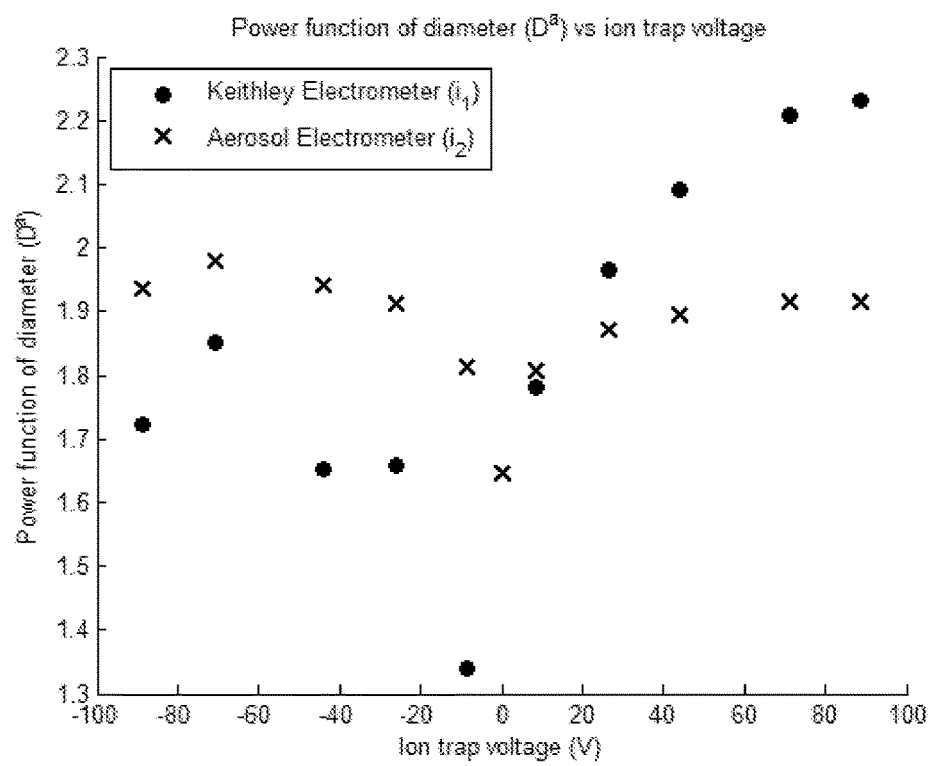
FIG. 12 is a graph of the particle diameter exponent β as a function of the applied potential difference between the first and second electrodes in the experimental sensor of FIG. 8.

FIG. 12 shows the calculated values of a normalised particle diameter exponent $$a = \frac{\beta_c}{\alpha_c}$$

(that is to say, the exponent is normalised such that the power of N in Equation (7) is 1) as a function of the applied potential difference using both the Keithley electrometer and the aerosol electrometer. The normalised exponent, a, is particularly sensitive to changes in the ion trap voltage. This means that the sensor may be calibrated such that, when the current is measured at two different trap voltages, both the particle concentration and the particle diameter may be independently determined.

Figure 13:
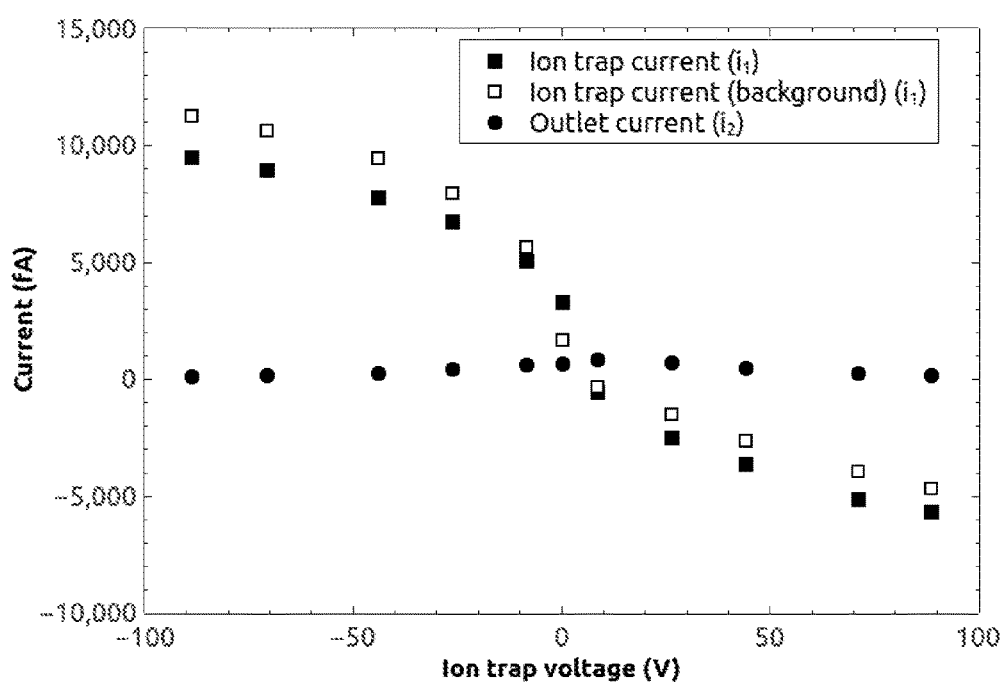
FIG. 13 is a graph of the electrode current and the collector current as a function of the applied potential difference between the first and second electrodes in the experimental sensor of FIG. 8, the graph further indicating the electrode current when no particles flow through the photoionisation chamber.
Figure 14:
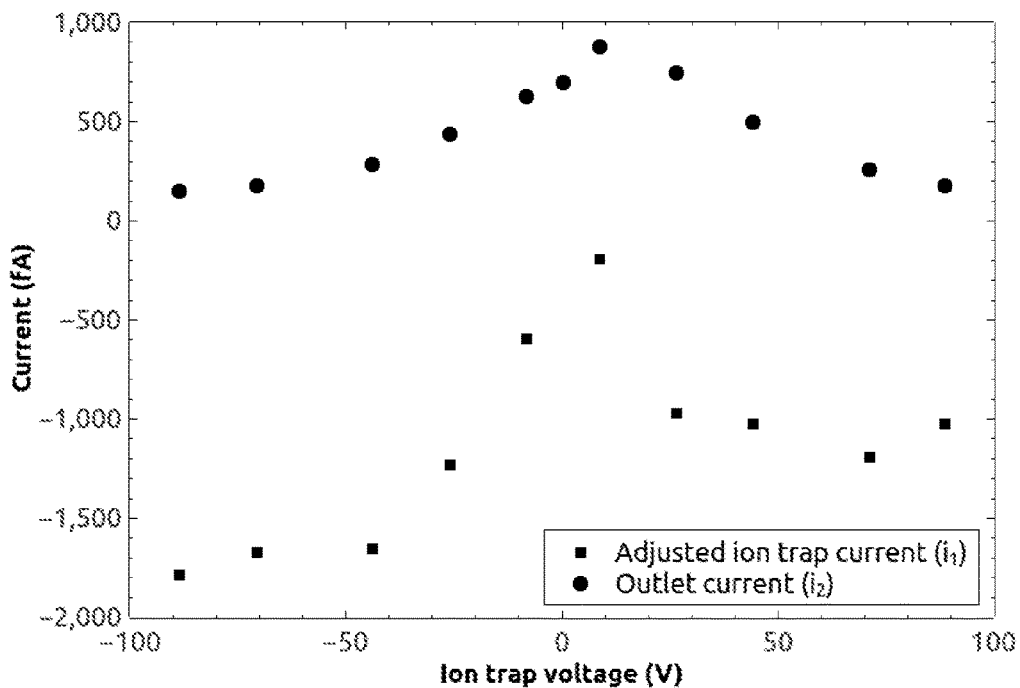
FIG. 14 is a graph of the collector current, and an electrode current compensated for background signal due to photoionisation chamber housing wall photoemission, as a function of applied potential difference between the first and second electrodes in the experimental sensor of FIG. 8.
Figure 15:
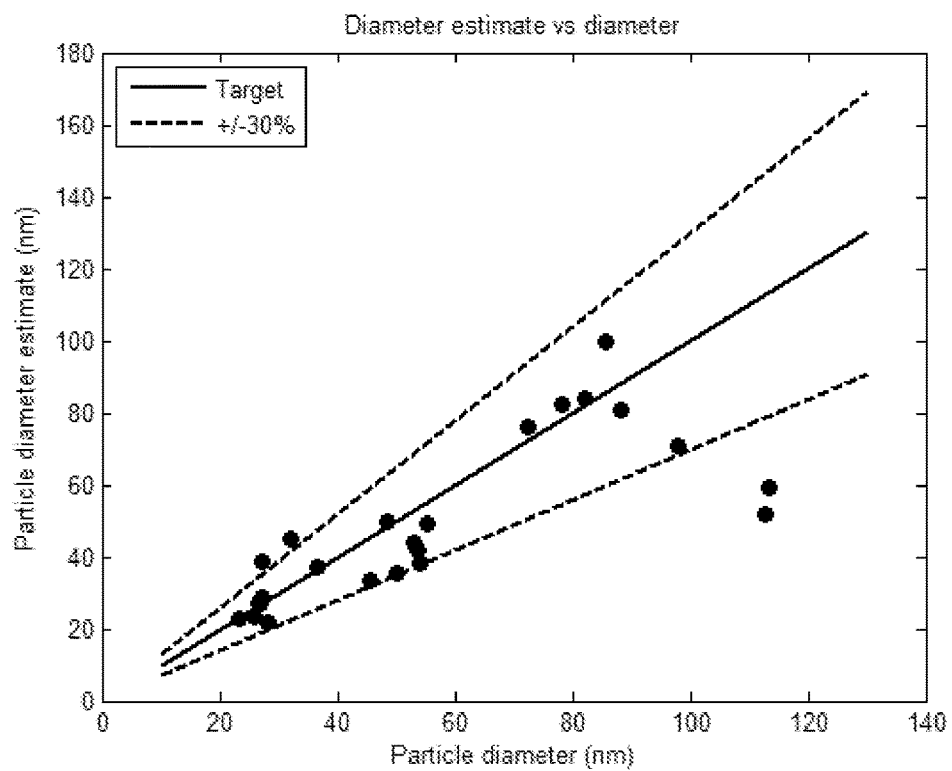
FIG. 15 compares the particle diameters estimated using the experimental sensor of FIG. 8 with the known particle diameters for a range of samples each having different particle diameters.

FIG. 13 shows the variation in the electrode current (i.e. the ion trap current) and the collector current (i.e. the outlet current) as a function of the ion trap voltage for a known particle distribution (N=1.64×10$^5$ cm$^{-3}$, mean D=47.9 nm). The collector current peaks at a low ion trap voltage as expected. The electrode current, however, continues to increase in magnitude with increasing ion trap voltage. This behaviour is also observed when no particles are present in the gas flow, indicated as the 'background current' in FIG. 13. The inventors believe that photoemission of electrons from photoemission chamber housing walls leading to negative ion formation in the gas is responsible for this observed behaviour. Electrons or gaseous ions, which would normally be likely to return to the same housing wall from which they are emitted, are instead drawn across the photoionisation chamber by the applied electric field and contribute to an increase in the electrode current. As shown in FIG. 14, the inventors have found that by subtracting the background signal from the measured electrode current, an adjusted electrode current which displays qualitatively similar behaviour to the collector current may be determined. The background signal may therefore be measured in an initial sensor calibration step, such that the measured electrode current may be compensated for housing wall photoemission during use of the sensor.

Figure 16:
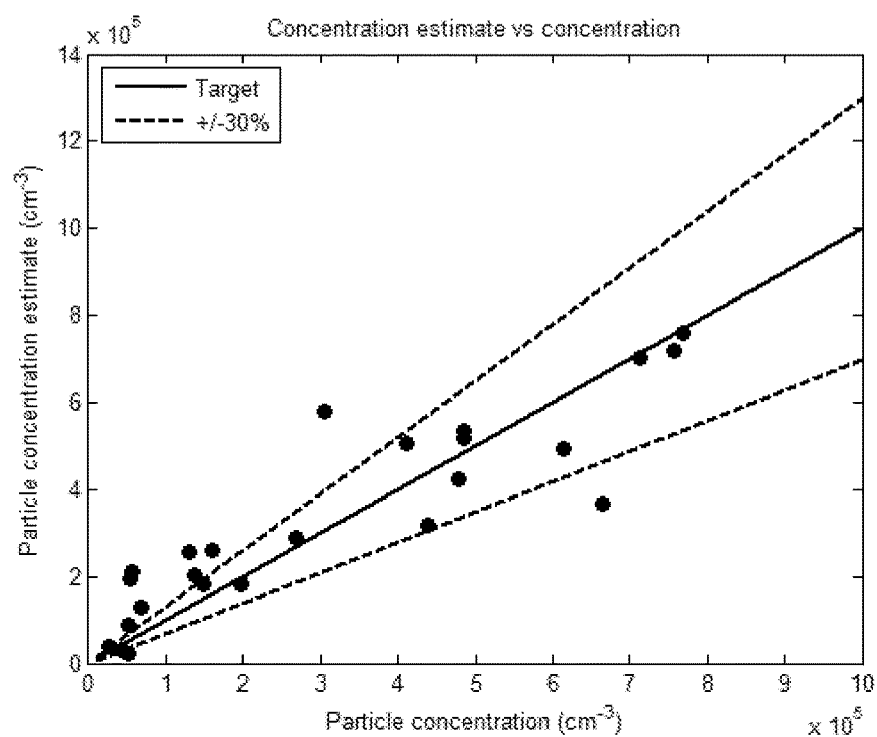
FIG. 16 compares the particle concentrations estimated using the experimental sensor of FIG. 8 with the known particle concentrations for a range of samples each having different particle concentrations.
Figure 17:
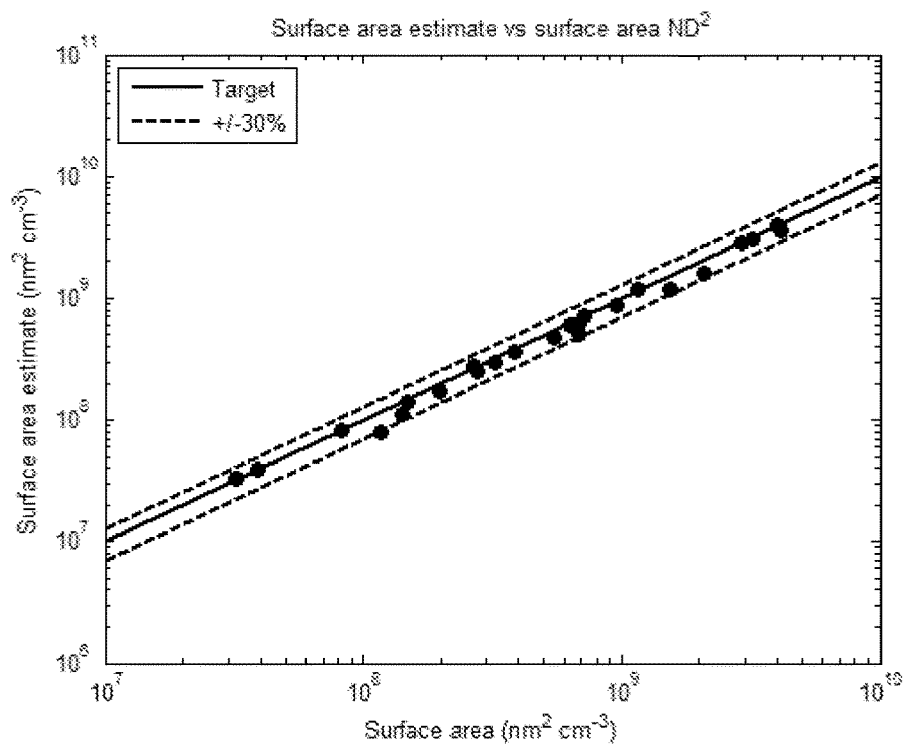
FIG. 17 compares the particle surface area estimated using the experimental sensor of FIG. 8 with the known particle surface area for a range of samples each having different particle surface areas.

Nevertheless, despite the large effect of housing wall photoemission which causes a significant non-zero electrode current to flow even at zero particle concentration, the electrode current does remain a function of particle concentration for all applied voltages tested (in a range of between 8.5 V and 88 V). It is therefore also possible to calibrate the sensor to output a measured particle concentration and diameter without explicitly determining the housing wall photoemission contribution to the electrode current or explicitly compensating the electrode current for this background contribution. For example, FIGS. 15, 16 and 17 respectively compare the particle diameters, concentrations and surface areas estimated using the experimental particle sensor with the known diameters, concentrations and surface areas for a range of samples. These initial results indicate that the estimated particle surface areas deviate by only up to ±30% from the surface areas determined by more precise methods. The spread in the independently estimated particle diameters and concentrations is only slightly greater.

The invention claimed is:

1. Particulate matter measurement apparatus comprising an inlet for receiving a gas sample for analysis, a photoionisation chamber, at least one light source arranged to illuminate an interior of the photoionisation chamber to photoionize particulate matter in the gas sample, first and second electrodes coupled to a power source and configured to provide a DC potential difference across at least a portion of the photoionisation chamber, and an outlet, together defining a gas flow path from the inlet, through the photoionisation chamber, and towards the outlet.

2. The apparatus of claim 1 further comprising at least one electrode current sensor configured to measure an electrode current flowing to or from at least one of the first and second electrodes.

3. The apparatus according to claim 2 further comprising a charged particulate matter detector and at least one detector current sensor configured to measure a detector current flowing from the charged particulate matter detector.

4. The apparatus according to claim 3 further comprising a comparator circuit configured to compare the electrode current, measured by the at least one electrode current sensor, and the detector current, measured by the at least one detector current sensor.

5. The apparatus according to claim 3 further comprising a processor configured to process the electrode current, measured by the at least one electrode current sensor, and the detector current, measured by the at least one detector current sensor, to determine a particulate matter concentration and/or size parameter of the particulate matter.

6. The apparatus of claim 3, further comprise a comparator circuit is configured to compare the electrode current, measured by the at least one electrode current sensor, and the detector current, measured by the at least one detector current sensor to determine a particulate matter concentration and/or size parameter of the particulate matter.

7. The apparatus according to claim 1, wherein the potential difference provided by the first and second electrodes is variable between at least first and second different DC voltages.

8. The apparatus according to claim 7, wherein the potential difference provided by the first and second electrodes is maintainable at each of the at least first and second different DC voltages for at least 0.5 seconds.

9. The apparatus according to claim 7, wherein the potential difference provided by the first and second electrodes is variable between the at least first and second different DC voltages at a frequency of less than 2 Hz.

10. The particulate measurement apparatus of claim 1 further comprising: a plurality of additional electrodes coupled to an additional power supply and configured to provide at least an additional potential difference across another portion of the photoionisation chamber concurrently with the potential difference provided across the portion of the photoionisation chamber.

11. The apparatus of claim 1, wherein the light source is an ultraviolet light source configured to emit ultraviolet light.

12. The apparatus of claim 1, wherein the light source is an ultraviolet light source configured to emit ultraviolet light within a range of 150 nm to 260 nm.

13. A method of using a particulate matter measurement apparatus, the method comprising:
receiving a gas sample for analysis using an inlet,
providing a photoionisation chamber, illuminating an interior of the photoionisation chamber using at least one light source to photoionize particulate matter in the gas sample;

coupling first and second electrodes to a power source to provide a DC potential difference across at least a portion of the photoionisation chamber, and providing an outlet, together defining a gas flow path from the inlet, through the photoionisation chamber, and towards the outlet.

14. The apparatus of claim 1, wherein the particulate matter is soot particles.

15. Particulate matter measurement apparatus comprising an inlet for receiving a gas sample for analysis, a photoionisation chamber, first and second electrodes, at least one light source arranged to illuminate an interior of the photoionisation chamber between the first and second electrodes to photoionize particulate matter in the gas sample, at least one electrode current sensor configured to measure an electrode current flowing to or from at least one of the first and second electrodes, and an outlet, together defining a gas flow path from the inlet, through the photoionisation chamber between the first and second electrodes, and towards the outlet.

16. The method according to claim 13 wherein the light source is an ultraviolet light source configured to emit ultraviolet light within a range of 150 nm to 260 nm.

17. The method of claim 16 applying another potential difference concurrently with the potential difference provided across the portion of the photoionisation chamber, by way of a plurality of additional electrodes, across another portion of the photoionisation chamber through which sample gas flows; and measuring one or more electrode currents flowing to or from at least one electrode from the plurality of additional electrodes.

18. The method of claim 16 further comprising measuring an electrode current flowing to or from at least one of the first and second electrodes using at least one electrode current sensor.

19. The method according to claim 18 further comprising providing a charged particulate matter detector and measuring a detector current flowing from the charged particulate matter detector using at least one detector current sensor.

20. The method according to claim 19 further comprising comparing, using a comparator circuit, the electrode current measured by the at least one electrode current sensor and the detector current measured by the at least one detector current sensor.

21. The method according to claim 20 further comprising using the electrode current measured by the at least one electrode current sensor and the detector current measured by the at least one detector current sensor to determine a particulate matter concentration and/or size parameter of the particulate matter.

22. The method according to claim 19 further comprising processing, using a processor, the electrode current, measured by the at least one electrode current sensor, and the detector current, measured by the at least one detector current sensor, to determine a particulate matter concentration and/or size parameter of the particulate matter.

23. The method according to claim 16, wherein the potential difference provided by the first and second electrodes is variable between at least first and second different DC voltages.

24. The method according to claim 23, wherein the potential difference provided by the first and second electrodes is maintainable at each of the at least first and second different DC voltages for at least 0.5 seconds.

25. The method according to claim 23, wherein the potential difference provided by the first and second electrodes is variable between the at least first and second different DC voltages at a frequency of less than 2 Hz.

26. The method according to claim 16 wherein the light source is an ultraviolet light source configured to emit ultraviolet light.

27. The method according to claim 16 wherein the particulate matter is soot particles.

* * * * *